United States Patent
Dhodapkar et al.

(10) Patent No.: US 9,846,162 B2
(45) Date of Patent: Dec. 19, 2017

(54) IMMUNE BIOMARKERS AND ASSAYS PREDICTIVE OF CLINICAL RESPONSE TO IMMUNOTHERAPY FOR CANCER

(71) Applicant: Yale University, New Haven, CT (US)

(72) Inventors: Madhav Dhodapkar, New Haven, CT (US); Kavita Dhodapkar, New Haven, CT (US)

(73) Assignee: Yale University, New Haven, CT (US)

( * ) Notice: Subject to any disclaimer, the term of this patent is extended or adjusted under 35 U.S.C. 154(b) by 43 days.

(21) Appl. No.: 14/401,360

(22) PCT Filed: Mar. 8, 2013

(86) PCT No.: PCT/US2013/029951
§ 371 (c)(1),
(2) Date: Nov. 14, 2014

(87) PCT Pub. No.: WO2013/172926
PCT Pub. Date: Nov. 21, 2013

(65) Prior Publication Data
US 2015/0140017 A1    May 21, 2015

Related U.S. Application Data

(60) Provisional application No. 61/646,541, filed on May 14, 2012.

(51) Int. Cl.
*A61K 39/00*    (2006.01)
*G01N 33/68*    (2006.01)
*G01N 33/574*   (2006.01)

(52) U.S. Cl.
CPC ... *G01N 33/6854* (2013.01); *G01N 33/57423* (2013.01); *G01N 2333/525* (2013.01); *G01N 2333/54* (2013.01); *G01N 2333/555* (2013.01); *G01N 2800/52* (2013.01)

(58) Field of Classification Search
None
See application file for complete search history.

(56) References Cited

U.S. PATENT DOCUMENTS

| | | |
|---|---|---|
| 2003/0092009 A1 | 5/2003 | Palm |
| 2009/0023174 A1 | 1/2009 | Manson |
| 2010/0129440 A1 | 5/2010 | Zhao et al. |
| 2010/0215647 A1 | 8/2010 | Pohlmann et al. |
| 2011/0274723 A1 | 11/2011 | Bot et al. |

OTHER PUBLICATIONS

Spisek et al, J Exp Med 204:831-840, 2007.*
Spisek et al, JEM, 204:831-840, 2007.*
Rutella et al, Clin and Dev immunolgoy 2012, article ID 196063, p. 1-13.*
Brahmer et al, N Eng J Med, 366:2455-65, Jun. 2, 2012.*
Diago et al, Gut. Mar. 2006;55(3):374-9. Epub Sep 8, 2005, abstract only.*
Bass et al, Nature Genetics, 41: 1238-1244, Nov 2009.*
Rosenblatt, et al., "PD-1 blockade by CT-011, anti PD-1 antibody, enhances ex-vivo T cell responses to autologous dendritic/myeloma fusion." 2012, J Immunother 34(5):409-418.
International Search Report and Written Opinion dated May 31, 2013, PCT Patent Application No. PCT/US13/29951, filed Mar. 8, 2013.
PCT International Search Report and Written Opinion for PCT/US2013/029951 dated May 31, 2013.
Rosenblatt, et al., "PD-1 blockade by CT-011, anti-PD-1 antibody, enhances ex vivo T-cell responses to autologous dendritic cell/myeloma fusion vaccine", J Immunother. 34(5), Jun. 2011, 409-418.

* cited by examiner

*Primary Examiner* — Lei Yao
(74) *Attorney, Agent, or Firm* — Saul Ewing Arnstein & Lehr LLP; Kathryn Doyle; Domingos J. Silva

(57) ABSTRACT

The present invention relates to predictors of a cancer patient's responsiveness to immunotherapy for cancer.

8 Claims, 9 Drawing Sheets

Squamus Cell Ca

Adenocarcinoma

Squamus Cell Ca

Adenocarcinoma

SEQUENCE LISTING

```
<160> NUMBER OF SEQ ID NOS: 134

<210> SEQ ID NO 1
<211> LENGTH: 14
<212> TYPE: PRT
<213> ORGANISM: Homo sapiens

<400> SEQUENCE: 1

His Ser Ala Arg Met Tyr Asn Met Met Glu Thr Glu Leu Lys
1               5                   10

<210> SEQ ID NO 2
<211> LENGTH: 14
<212> TYPE: PRT
<213> ORGANISM: Homo sapiens

<400> SEQUENCE: 2

Arg Met Tyr Asn Met Met Glu Thr Glu Leu Lys Pro Pro Gly
1               5                   10

<210> SEQ ID NO 3
<211> LENGTH: 15
<212> TYPE: PRT
<213> ORGANISM: Homo sapiens

<400> SEQUENCE: 3

Asn Met Met Glu Thr Glu Leu Lys Pro Pro Gly Pro Gln Gln Thr
1               5                   10                  15

<210> SEQ ID NO 4
<211> LENGTH: 15
<212> TYPE: PRT
<213> ORGANISM: Homo sapiens

<400> SEQUENCE: 4

Thr Glu Leu Lys Pro Pro Gly Pro Gln Gln Thr Ser Gly Gly Gly
1               5                   10                  15

<210> SEQ ID NO 5
<211> LENGTH: 15
<212> TYPE: PRT
<213> ORGANISM: Homo sapiens

<400> SEQUENCE: 5

Pro Pro Gly Pro Gln Gln Thr Ser Gly Gly Gly Gly Asn Ser
1               5                   10                  15

<210> SEQ ID NO 6
```

```
<211> LENGTH: 15
<212> TYPE: PRT
<213> ORGANISM: Homo sapiens

<400> SEQUENCE: 6

Pro Gln Gln Thr Ser Gly Gly Gly Gly Asn Ser Thr Ala Ala
1               5                   10                  15

<210> SEQ ID NO 7
<211> LENGTH: 15
<212> TYPE: PRT
<213> ORGANISM: Homo sapiens

<400> SEQUENCE: 7

Ser Gly Gly Gly Gly Gly Asn Ser Thr Ala Ala Ala Ala Gly Gly
1               5                   10                  15

<210> SEQ ID NO 8
<211> LENGTH: 14
<212> TYPE: PRT
<213> ORGANISM: Homo sapiens

<400> SEQUENCE: 8

Gly Gly Asn Ser Thr Ala Ala Ala Ala Gly Gly Asn Gln Lys
1               5                   10

<210> SEQ ID NO 9
<211> LENGTH: 13
<212> TYPE: PRT
<213> ORGANISM: Homo sapiens

<400> SEQUENCE: 9

Ser Thr Ala Ala Ala Ala Gly Gly Asn Gln Lys Asn Ser
1               5                   10

<210> SEQ ID NO 10
<211> LENGTH: 15
<212> TYPE: PRT
<213> ORGANISM: Homo sapiens

<400> SEQUENCE: 10

Ala Ala Ala Ala Gly Gly Asn Gln Lys Asn Ser Pro Asp Arg Val
1               5                   10                  15

<210> SEQ ID NO 11
<211> LENGTH: 15
<212> TYPE: PRT
<213> ORGANISM: Homo sapiens

<400> SEQUENCE: 11

Gly Gly Asn Gln Lys Asn Ser Pro Asp Arg Val Lys Arg Pro Met
1               5                   10                  15

<210> SEQ ID NO 12
<211> LENGTH: 15
<212> TYPE: PRT
<213> ORGANISM: Homo sapiens

<400> SEQUENCE: 12

Lys Asn Ser Pro Asp Arg Val Lys Arg Pro Met Asn Ala Phe Met
1               5                   10                  15

<210> SEQ ID NO 13
<211> LENGTH: 15
<212> TYPE: PRT
```

<213> ORGANISM: Homo sapiens

<400> SEQUENCE: 13

Asp Arg Val Lys Arg Pro Met Asn Ala Phe Met Val Trp Ser Arg
1               5                   10                  15

<210> SEQ ID NO 14
<211> LENGTH: 15
<212> TYPE: PRT
<213> ORGANISM: Homo sapiens

<400> SEQUENCE: 14

Arg Pro Met Asn Ala Phe Met Val Trp Ser Arg Gly Gln Arg Arg
1               5                   10                  15

<210> SEQ ID NO 15
<211> LENGTH: 14
<212> TYPE: PRT
<213> ORGANISM: Homo sapiens

<400> SEQUENCE: 15

Ala Phe Met Val Trp Ser Arg Gly Gln Arg Arg Lys Met Ala
1               5                   10

<210> SEQ ID NO 16
<211> LENGTH: 16
<212> TYPE: PRT
<213> ORGANISM: Homo sapiens

<400> SEQUENCE: 16

Val Trp Ser Arg Gly Gln Arg Arg Lys Met Ala Gln Glu Asn Pro Lys
1               5                   10                  15

<210> SEQ ID NO 17
<211> LENGTH: 14
<212> TYPE: PRT
<213> ORGANISM: Homo sapiens

<400> SEQUENCE: 17

Gly Gln Arg Arg Lys Met Ala Gln Glu Asn Pro Lys Met His
1               5                   10

<210> SEQ ID NO 18
<211> LENGTH: 15
<212> TYPE: PRT
<213> ORGANISM: Homo sapiens

<400> SEQUENCE: 18

Arg Lys Met Ala Gln Glu Asn Pro Lys Met His Asn Ser Glu Ile
1               5                   10                  15

<210> SEQ ID NO 19
<211> LENGTH: 15
<212> TYPE: PRT
<213> ORGANISM: Homo sapiens

<400> SEQUENCE: 19

Ala Gln Glu Asn Pro Lys Met His Asn Ser Glu Ile Ser Lys Arg
1               5                   10                  15

<210> SEQ ID NO 20
<211> LENGTH: 14
<212> TYPE: PRT
<213> ORGANISM: Homo sapiens

```
<400> SEQUENCE: 20

Pro Lys Met His Asn Ser Glu Ile Ser Lys Arg Leu Gly Ala
1               5                   10

<210> SEQ ID NO 21
<211> LENGTH: 15
<212> TYPE: PRT
<213> ORGANISM: Homo sapiens

<400> SEQUENCE: 21

His Asn Ser Glu Ile Ser Lys Arg Leu Gly Ala Glu Trp Lys Leu
1               5                   10                  15

<210> SEQ ID NO 22
<211> LENGTH: 15
<212> TYPE: PRT
<213> ORGANISM: Homo sapiens

<400> SEQUENCE: 22

Ile Ser Lys Arg Leu Gly Ala Glu Trp Lys Leu Leu Ser Glu Thr
1               5                   10                  15

<210> SEQ ID NO 23
<211> LENGTH: 14
<212> TYPE: PRT
<213> ORGANISM: Homo sapiens

<400> SEQUENCE: 23

Leu Gly Ala Glu Trp Lys Leu Leu Ser Glu Thr Glu Lys Arg
1               5                   10

<210> SEQ ID NO 24
<211> LENGTH: 14
<212> TYPE: PRT
<213> ORGANISM: Homo sapiens

<400> SEQUENCE: 24

Glu Trp Lys Leu Leu Ser Glu Thr Glu Lys Arg Pro Phe Ile
1               5                   10

<210> SEQ ID NO 25
<211> LENGTH: 15
<212> TYPE: PRT
<213> ORGANISM: Homo sapiens

<400> SEQUENCE: 25

Leu Leu Ser Glu Thr Glu Lys Arg Pro Phe Ile Asp Glu Ala Lys
1               5                   10                  15

<210> SEQ ID NO 26
<211> LENGTH: 15
<212> TYPE: PRT
<213> ORGANISM: Homo sapiens

<400> SEQUENCE: 26

Thr Glu Lys Arg Pro Phe Ile Asp Glu Ala Lys Arg Leu Arg Ala
1               5                   10                  15

<210> SEQ ID NO 27
<211> LENGTH: 15
<212> TYPE: PRT
<213> ORGANISM: Homo sapiens

<400> SEQUENCE: 27
```

```
Pro Phe Ile Asp Glu Ala Lys Arg Leu Arg Ala Leu His Met Lys
1               5                   10                  15
```

<210> SEQ ID NO 28
<211> LENGTH: 13
<212> TYPE: PRT
<213> ORGANISM: Homo sapiens

<400> SEQUENCE: 28

```
Glu Ala Lys Arg Leu Arg Ala Leu His Met Lys Glu His
1               5                   10
```

<210> SEQ ID NO 29
<211> LENGTH: 15
<212> TYPE: PRT
<213> ORGANISM: Homo sapiens

<400> SEQUENCE: 29

```
Lys Arg Leu Arg Ala Leu His Met Lys Glu His Pro Asp Tyr Lys
1               5                   10                  15
```

<210> SEQ ID NO 30
<211> LENGTH: 15
<212> TYPE: PRT
<213> ORGANISM: Homo sapiens

<400> SEQUENCE: 30

```
Ala Leu His Met Lys Glu His Pro Asp Tyr Lys Tyr Arg Pro Arg
1               5                   10                  15
```

<210> SEQ ID NO 31
<211> LENGTH: 15
<212> TYPE: PRT
<213> ORGANISM: Homo sapiens

<400> SEQUENCE: 31

```
Lys Glu His Pro Asp Tyr Lys Tyr Arg Pro Arg Lys Thr Lys
1               5                   10                  15
```

<210> SEQ ID NO 32
<211> LENGTH: 15
<212> TYPE: PRT
<213> ORGANISM: Homo sapiens

<400> SEQUENCE: 32

```
Asp Tyr Lys Tyr Arg Pro Arg Lys Thr Lys Thr Leu Met Lys
1               5                   10                  15
```

<210> SEQ ID NO 33
<211> LENGTH: 15
<212> TYPE: PRT
<213> ORGANISM: Homo sapiens

<400> SEQUENCE: 33

```
Arg Pro Arg Arg Lys Thr Lys Thr Leu Met Lys Lys Asp Lys Tyr
1               5                   10                  15
```

<210> SEQ ID NO 34
<211> LENGTH: 15
<212> TYPE: PRT
<213> ORGANISM: Homo sapiens

<400> SEQUENCE: 34

```
Lys Thr Lys Thr Leu Met Lys Lys Asp Lys Tyr Thr Leu Pro Gly
1               5                   10                  15
```

<210> SEQ ID NO 35
<211> LENGTH: 15
<212> TYPE: PRT
<213> ORGANISM: Homo sapiens

<400> SEQUENCE: 35

```
Leu Met Lys Lys Asp Lys Tyr Thr Leu Pro Gly Gly Leu Leu Ala
1               5                   10                  15
```

<210> SEQ ID NO 36
<211> LENGTH: 14
<212> TYPE: PRT
<213> ORGANISM: Homo sapiens

<400> SEQUENCE: 36

```
Asp Lys Tyr Thr Leu Pro Gly Gly Leu Leu Ala Pro Gly Gly
1               5                   10
```

<210> SEQ ID NO 37
<211> LENGTH: 15
<212> TYPE: PRT
<213> ORGANISM: Homo sapiens

<400> SEQUENCE: 37

```
Thr Leu Pro Gly Gly Leu Leu Ala Pro Gly Gly Asn Ser Met Ala
1               5                   10                  15
```

<210> SEQ ID NO 38
<211> LENGTH: 15
<212> TYPE: PRT
<213> ORGANISM: Homo sapiens

<400> SEQUENCE: 38

```
Gly Leu Leu Ala Pro Gly Gly Asn Ser Met Ala Ser Gly Val Gly
1               5                   10                  15
```

<210> SEQ ID NO 39
<211> LENGTH: 15
<212> TYPE: PRT
<213> ORGANISM: Homo sapiens

<400> SEQUENCE: 39

```
Pro Gly Gly Asn Ser Met Ala Ser Gly Val Gly Val Gly Ala Gly
1               5                   10                  15
```

<210> SEQ ID NO 40
<211> LENGTH: 15
<212> TYPE: PRT
<213> ORGANISM: Homo sapiens

<400> SEQUENCE: 40

```
Ser Met Ala Ser Gly Val Gly Val Gly Ala Gly Leu Gly Ala Gly
1               5                   10                  15
```

<210> SEQ ID NO 41
<211> LENGTH: 15
<212> TYPE: PRT
<213> ORGANISM: Homo sapiens

<400> SEQUENCE: 41

```
Gly Val Gly Val Gly Ala Gly Leu Gly Ala Gly Val Asn Gln Arg
1               5                   10                  15
```

-continued

```
<210> SEQ ID NO 42
<211> LENGTH: 15
<212> TYPE: PRT
<213> ORGANISM: Homo sapiens

<400> SEQUENCE: 42

Gly Ala Gly Leu Gly Ala Gly Val Asn Gln Arg Met Asp Ser Tyr
1               5                   10                  15

<210> SEQ ID NO 43
<211> LENGTH: 14
<212> TYPE: PRT
<213> ORGANISM: Homo sapiens

<400> SEQUENCE: 43

Gly Ala Gly Val Asn Gln Arg Met Asp Ser Tyr Ala His Met
1               5                   10

<210> SEQ ID NO 44
<211> LENGTH: 15
<212> TYPE: PRT
<213> ORGANISM: Homo sapiens

<400> SEQUENCE: 44

Val Asn Gln Arg Met Asp Ser Tyr Ala His Met Asn Gly Trp Ser
1               5                   10                  15

<210> SEQ ID NO 45
<211> LENGTH: 15
<212> TYPE: PRT
<213> ORGANISM: Homo sapiens

<400> SEQUENCE: 45

Met Asp Ser Tyr Ala His Met Asn Gly Trp Ser Asn Gly Ser Tyr
1               5                   10                  15

<210> SEQ ID NO 46
<211> LENGTH: 14
<212> TYPE: PRT
<213> ORGANISM: Homo sapiens

<400> SEQUENCE: 46

Ala His Met Asn Gly Trp Ser Asn Gly Ser Tyr Ser Met Met
1               5                   10

<210> SEQ ID NO 47
<211> LENGTH: 15
<212> TYPE: PRT
<213> ORGANISM: Homo sapiens

<400> SEQUENCE: 47

Asn Gly Trp Ser Asn Gly Ser Tyr Ser Met Met Gln Asp Gln Leu
1               5                   10                  15

<210> SEQ ID NO 48
<211> LENGTH: 13
<212> TYPE: PRT
<213> ORGANISM: Homo sapiens

<400> SEQUENCE: 48

Asn Gly Ser Tyr Ser Met Met Gln Asp Gln Leu Gly Tyr
1               5                   10

<210> SEQ ID NO 49
<211> LENGTH: 14
```

```
<212> TYPE: PRT
<213> ORGANISM: Homo sapiens

<400> SEQUENCE: 49

Ser Tyr Ser Met Met Gln Asp Gln Leu Gly Tyr Pro Gln His
1               5                   10

<210> SEQ ID NO 50
<211> LENGTH: 14
<212> TYPE: PRT
<213> ORGANISM: Homo sapiens

<400> SEQUENCE: 50

Met Met Gln Asp Gln Leu Gly Tyr Pro Gln His Pro Gly Leu
1               5                   10

<210> SEQ ID NO 51
<211> LENGTH: 15
<212> TYPE: PRT
<213> ORGANISM: Homo sapiens

<400> SEQUENCE: 51

Asp Gln Leu Gly Tyr Pro Gln His Pro Gly Leu Asn Ala His Gly
1               5                   10                  15

<210> SEQ ID NO 52
<211> LENGTH: 15
<212> TYPE: PRT
<213> ORGANISM: Homo sapiens

<400> SEQUENCE: 52

Tyr Pro Gln His Pro Gly Leu Asn Ala His Gly Ala Ala Gln Met
1               5                   10                  15

<210> SEQ ID NO 53
<211> LENGTH: 15
<212> TYPE: PRT
<213> ORGANISM: Homo sapiens

<400> SEQUENCE: 53

Pro Gly Leu Asn Ala His Gly Ala Ala Gln Met Gln Pro Met His
1               5                   10                  15

<210> SEQ ID NO 54
<211> LENGTH: 15
<212> TYPE: PRT
<213> ORGANISM: Homo sapiens

<400> SEQUENCE: 54

Ala His Gly Ala Ala Gln Met Gln Pro Met His Arg Tyr Asp Val
1               5                   10                  15

<210> SEQ ID NO 55
<211> LENGTH: 14
<212> TYPE: PRT
<213> ORGANISM: Homo sapiens

<400> SEQUENCE: 55

Ala Gln Met Gln Pro Met His Arg Tyr Asp Val Ser Ala Leu
1               5                   10

<210> SEQ ID NO 56
<211> LENGTH: 14
<212> TYPE: PRT
<213> ORGANISM: Homo sapiens
```

<400> SEQUENCE: 56

Met Gln Pro Met His Arg Tyr Asp Val Ser Ala Leu Gln Tyr
1               5                   10

<210> SEQ ID NO 57
<211> LENGTH: 15
<212> TYPE: PRT
<213> ORGANISM: Homo sapiens

<400> SEQUENCE: 57

Met His Arg Tyr Asp Val Ser Ala Leu Gln Tyr Asn Ser Met Thr
1               5                   10                  15

<210> SEQ ID NO 58
<211> LENGTH: 15
<212> TYPE: PRT
<213> ORGANISM: Homo sapiens

<400> SEQUENCE: 58

Asp Val Ser Ala Leu Gln Tyr Asn Ser Met Thr Ser Ser Gln Thr
1               5                   10                  15

<210> SEQ ID NO 59
<211> LENGTH: 15
<212> TYPE: PRT
<213> ORGANISM: Homo sapiens

<400> SEQUENCE: 59

Leu Gln Tyr Asn Ser Met Thr Ser Ser Gln Thr Tyr Met Asn Gly
1               5                   10                  15

<210> SEQ ID NO 60
<211> LENGTH: 15
<212> TYPE: PRT
<213> ORGANISM: Homo sapiens

<400> SEQUENCE: 60

Ser Met Thr Ser Ser Gln Thr Tyr Met Asn Gly Ser Pro Thr Tyr
1               5                   10                  15

<210> SEQ ID NO 61
<211> LENGTH: 15
<212> TYPE: PRT
<213> ORGANISM: Homo sapiens

<400> SEQUENCE: 61

Ser Gln Thr Tyr Met Asn Gly Ser Pro Thr Tyr Ser Met Ser Tyr
1               5                   10                  15

<210> SEQ ID NO 62
<211> LENGTH: 15
<212> TYPE: PRT
<213> ORGANISM: Homo sapiens

<400> SEQUENCE: 62

Met Asn Gly Ser Pro Thr Tyr Ser Met Ser Tyr Ser Gln Gln Gly
1               5                   10                  15

<210> SEQ ID NO 63
<211> LENGTH: 15
<212> TYPE: PRT
<213> ORGANISM: Homo sapiens

<400> SEQUENCE: 63

Pro Thr Tyr Ser Met Ser Tyr Ser Gln Gln Gly Thr Pro Gly Met
1               5                   10                  15

<210> SEQ ID NO 64
<211> LENGTH: 15
<212> TYPE: PRT
<213> ORGANISM: Homo sapiens

<400> SEQUENCE: 64

Met Ser Tyr Ser Gln Gln Gly Thr Pro Gly Met Ala Leu Gly Ser
1               5                   10                  15

<210> SEQ ID NO 65
<211> LENGTH: 15
<212> TYPE: PRT
<213> ORGANISM: Homo sapiens

<400> SEQUENCE: 65

Ser Gln Gln Gly Thr Pro Gly Met Ala Leu Gly Ser Met Gly Ser
1               5                   10                  15

<210> SEQ ID NO 66
<211> LENGTH: 15
<212> TYPE: PRT
<213> ORGANISM: Homo sapiens

<400> SEQUENCE: 66

Thr Pro Gly Met Ala Leu Gly Ser Met Gly Ser Val Val Lys Ser
1               5                   10                  15

<210> SEQ ID NO 67
<211> LENGTH: 15
<212> TYPE: PRT
<213> ORGANISM: Homo sapiens

<400> SEQUENCE: 67

Ala Leu Gly Ser Met Gly Ser Val Val Lys Ser Glu Ala Ser Ser
1               5                   10                  15

<210> SEQ ID NO 68
<211> LENGTH: 15
<212> TYPE: PRT
<213> ORGANISM: Homo sapiens

<400> SEQUENCE: 68

Met Gly Ser Val Val Lys Ser Glu Ala Ser Ser Ser Pro Pro Val
1               5                   10                  15

<210> SEQ ID NO 69
<211> LENGTH: 15
<212> TYPE: PRT
<213> ORGANISM: Homo sapiens

<400> SEQUENCE: 69

Val Lys Ser Glu Ala Ser Ser Ser Pro Pro Val Val Thr Ser Ser
1               5                   10                  15

<210> SEQ ID NO 70
<211> LENGTH: 15
<212> TYPE: PRT
<213> ORGANISM: Homo sapiens

<400> SEQUENCE: 70

Ala Ser Ser Ser Pro Pro Val Val Thr Ser Ser Ser His Ser Arg

```
<210> SEQ ID NO 71
<211> LENGTH: 12
<212> TYPE: PRT
<213> ORGANISM: Homo sapiens

<400> SEQUENCE: 71

Pro Pro Val Val Thr Ser Ser His Ser Arg Ala
1               5                   10

<210> SEQ ID NO 72
<211> LENGTH: 15
<212> TYPE: PRT
<213> ORGANISM: Homo sapiens

<400> SEQUENCE: 72

Pro Val Val Thr Ser Ser His Ser Arg Ala Pro Cys Gln Ala
1               5                   10                  15

<210> SEQ ID NO 73
<211> LENGTH: 15
<212> TYPE: PRT
<213> ORGANISM: Homo sapiens

<400> SEQUENCE: 73

Ser Ser Ser His Ser Arg Ala Pro Cys Gln Ala Gly Asp Leu Arg
1               5                   10                  15

<210> SEQ ID NO 74
<211> LENGTH: 15
<212> TYPE: PRT
<213> ORGANISM: Homo sapiens

<400> SEQUENCE: 74

Ser Arg Ala Pro Cys Gln Ala Gly Asp Leu Arg Asp Met Ile Ser
1               5                   10                  15

<210> SEQ ID NO 75
<211> LENGTH: 14
<212> TYPE: PRT
<213> ORGANISM: Homo sapiens

<400> SEQUENCE: 75

Cys Gln Ala Gly Asp Leu Arg Asp Met Ile Ser Met Tyr Leu
1               5                   10

<210> SEQ ID NO 76
<211> LENGTH: 14
<212> TYPE: PRT
<213> ORGANISM: Homo sapiens

<400> SEQUENCE: 76

Gly Asp Leu Arg Asp Met Ile Ser Met Tyr Leu Pro Gly Ala
1               5                   10

<210> SEQ ID NO 77
<211> LENGTH: 13
<212> TYPE: PRT
<213> ORGANISM: Homo sapiens

<400> SEQUENCE: 77

Arg Asp Met Ile Ser Met Tyr Leu Pro Gly Ala Glu Val
1               5                   10
```

<210> SEQ ID NO 78
<211> LENGTH: 15
<212> TYPE: PRT
<213> ORGANISM: Homo sapiens

<400> SEQUENCE: 78

Met Ile Ser Met Tyr Leu Pro Gly Ala Glu Val Pro Glu Pro Ala
1               5                   10                  15

<210> SEQ ID NO 79
<211> LENGTH: 15
<212> TYPE: PRT
<213> ORGANISM: Homo sapiens

<400> SEQUENCE: 79

Tyr Leu Pro Gly Ala Glu Val Pro Glu Pro Ala Ala Pro Ser Arg
1               5                   10                  15

<210> SEQ ID NO 80
<211> LENGTH: 15
<212> TYPE: PRT
<213> ORGANISM: Homo sapiens

<400> SEQUENCE: 80

Ala Glu Val Pro Glu Pro Ala Ala Pro Ser Arg Leu His Met Ser
1               5                   10                  15

<210> SEQ ID NO 81
<211> LENGTH: 14
<212> TYPE: PRT
<213> ORGANISM: Homo sapiens

<400> SEQUENCE: 81

Glu Pro Ala Ala Pro Ser Arg Leu His Met Ser Gln His Tyr
1               5                   10

<210> SEQ ID NO 82
<211> LENGTH: 14
<212> TYPE: PRT
<213> ORGANISM: Homo sapiens

<400> SEQUENCE: 82

Ala Pro Ser Arg Leu His Met Ser Gln His Tyr Gln Ser Gly
1               5                   10

<210> SEQ ID NO 83
<211> LENGTH: 15
<212> TYPE: PRT
<213> ORGANISM: Homo sapiens

<400> SEQUENCE: 83

Arg Leu His Met Ser Gln His Tyr Gln Ser Gly Pro Val Pro Gly
1               5                   10                  15

<210> SEQ ID NO 84
<211> LENGTH: 14
<212> TYPE: PRT
<213> ORGANISM: Homo sapiens

<400> SEQUENCE: 84

Ser Gln His Tyr Gln Ser Gly Pro Val Pro Gly Thr Ala Ile
1               5                   10

<210> SEQ ID NO 85

```
<211> LENGTH: 15
<212> TYPE: PRT
<213> ORGANISM: Homo sapiens

<400> SEQUENCE: 85

Tyr Gln Ser Gly Pro Val Pro Gly Thr Ala Ile Asn Gly Thr Leu
1               5                   10                  15

<210> SEQ ID NO 86
<211> LENGTH: 16
<212> TYPE: PRT
<213> ORGANISM: Homo sapiens

<400> SEQUENCE: 86

Pro Val Pro Gly Thr Ala Ile Asn Gly Thr Leu Pro Leu Ser His Met
1               5                   10                  15

<210> SEQ ID NO 87
<211> LENGTH: 15
<212> TYPE: PRT
<213> ORGANISM: Homo sapiens

<400> SEQUENCE: 87

Met Gln Ala Glu Gly Arg Gly Thr Gly Ser Thr Gly Asp Ala
1               5                   10                  15

<210> SEQ ID NO 88
<211> LENGTH: 15
<212> TYPE: PRT
<213> ORGANISM: Homo sapiens

<400> SEQUENCE: 88

Gly Arg Gly Thr Gly Gly Ser Thr Gly Asp Ala Asp Gly Pro Gly
1               5                   10                  15

<210> SEQ ID NO 89
<211> LENGTH: 15
<212> TYPE: PRT
<213> ORGANISM: Homo sapiens

<400> SEQUENCE: 89

Gly Gly Ser Thr Gly Asp Ala Asp Gly Pro Gly Gly Pro Gly Ile
1               5                   10                  15

<210> SEQ ID NO 90
<211> LENGTH: 14
<212> TYPE: PRT
<213> ORGANISM: Homo sapiens

<400> SEQUENCE: 90

Gly Asp Ala Asp Gly Pro Gly Gly Pro Gly Ile Pro Asp Gly
1               5                   10

<210> SEQ ID NO 91
<211> LENGTH: 14
<212> TYPE: PRT
<213> ORGANISM: Homo sapiens

<400> SEQUENCE: 91

Asp Gly Pro Gly Gly Pro Gly Ile Pro Asp Gly Pro Gly Gly
1               5                   10

<210> SEQ ID NO 92
<211> LENGTH: 15
<212> TYPE: PRT
```

-continued

<213> ORGANISM: Homo sapiens

<400> SEQUENCE: 92

Gly Gly Pro Gly Ile Pro Asp Gly Pro Gly Gly Asn Ala Gly Gly
1               5                   10                  15

<210> SEQ ID NO 93
<211> LENGTH: 15
<212> TYPE: PRT
<213> ORGANISM: Homo sapiens

<400> SEQUENCE: 93

Ile Pro Asp Gly Pro Gly Gly Asn Ala Gly Gly Pro Gly Glu Ala
1               5                   10                  15

<210> SEQ ID NO 94
<211> LENGTH: 15
<212> TYPE: PRT
<213> ORGANISM: Homo sapiens

<400> SEQUENCE: 94

Pro Gly Gly Asn Ala Gly Gly Pro Gly Glu Ala Gly Ala Thr Gly
1               5                   10                  15

<210> SEQ ID NO 95
<211> LENGTH: 14
<212> TYPE: PRT
<213> ORGANISM: Homo sapiens

<400> SEQUENCE: 95

Ala Gly Gly Pro Gly Glu Ala Gly Ala Thr Gly Gly Arg Gly
1               5                   10

<210> SEQ ID NO 96
<211> LENGTH: 15
<212> TYPE: PRT
<213> ORGANISM: Homo sapiens

<400> SEQUENCE: 96

Pro Gly Glu Ala Gly Ala Thr Gly Gly Arg Gly Pro Arg Gly Ala
1               5                   10                  15

<210> SEQ ID NO 97
<211> LENGTH: 15
<212> TYPE: PRT
<213> ORGANISM: Homo sapiens

<400> SEQUENCE: 97

Gly Ala Thr Gly Gly Arg Gly Pro Arg Gly Ala Gly Ala Ala Arg
1               5                   10                  15

<210> SEQ ID NO 98
<211> LENGTH: 14
<212> TYPE: PRT
<213> ORGANISM: Homo sapiens

<400> SEQUENCE: 98

Gly Arg Gly Pro Arg Gly Ala Gly Ala Ala Arg Ala Ser Gly
1               5                   10

<210> SEQ ID NO 99
<211> LENGTH: 15
<212> TYPE: PRT
<213> ORGANISM: Homo sapiens

```
<400> SEQUENCE: 99

Pro Arg Gly Ala Gly Ala Ala Arg Ala Ser Gly Pro Gly Gly Gly
1               5                   10                  15

<210> SEQ ID NO 100
<211> LENGTH: 15
<212> TYPE: PRT
<213> ORGANISM: Homo sapiens

<400> SEQUENCE: 100

Gly Ala Ala Arg Ala Ser Gly Pro Gly Gly Gly Ala Pro Arg Gly
1               5                   10                  15

<210> SEQ ID NO 101
<211> LENGTH: 15
<212> TYPE: PRT
<213> ORGANISM: Homo sapiens

<400> SEQUENCE: 101

Ala Ser Gly Pro Gly Gly Gly Ala Pro Arg Gly Pro His Gly Gly
1               5                   10                  15

<210> SEQ ID NO 102
<211> LENGTH: 15
<212> TYPE: PRT
<213> ORGANISM: Homo sapiens

<400> SEQUENCE: 102

Gly Gly Gly Ala Pro Arg Gly Pro His Gly Gly Ala Ala Ser Gly
1               5                   10                  15

<210> SEQ ID NO 103
<211> LENGTH: 14
<212> TYPE: PRT
<213> ORGANISM: Homo sapiens

<400> SEQUENCE: 103

Pro Arg Gly Pro His Gly Gly Ala Ala Ser Gly Leu Asn Gly
1               5                   10

<210> SEQ ID NO 104
<211> LENGTH: 14
<212> TYPE: PRT
<213> ORGANISM: Homo sapiens

<400> SEQUENCE: 104

Pro His Gly Gly Ala Ala Ser Gly Leu Asn Gly Cys Cys Arg
1               5                   10

<210> SEQ ID NO 105
<211> LENGTH: 15
<212> TYPE: PRT
<213> ORGANISM: Homo sapiens

<400> SEQUENCE: 105

Gly Ala Ala Ser Gly Leu Asn Gly Cys Cys Arg Cys Gly Ala Arg
1               5                   10                  15

<210> SEQ ID NO 106
<211> LENGTH: 15
<212> TYPE: PRT
<213> ORGANISM: Homo sapiens

<400> SEQUENCE: 106
```

Gly Leu Asn Gly Cys Cys Arg Cys Gly Ala Arg Gly Pro Glu Ser
1               5                   10                  15

<210> SEQ ID NO 107
<211> LENGTH: 14
<212> TYPE: PRT
<213> ORGANISM: Homo sapiens

<400> SEQUENCE: 107

Cys Cys Arg Cys Gly Ala Arg Gly Pro Glu Ser Arg Leu Leu
1               5                   10

<210> SEQ ID NO 108
<211> LENGTH: 15
<212> TYPE: PRT
<213> ORGANISM: Homo sapiens

<400> SEQUENCE: 108

Cys Gly Ala Arg Gly Pro Glu Ser Arg Leu Leu Glu Phe Tyr Leu
1               5                   10                  15

<210> SEQ ID NO 109
<211> LENGTH: 15
<212> TYPE: PRT
<213> ORGANISM: Homo sapiens

<400> SEQUENCE: 109

Gly Pro Glu Ser Arg Leu Leu Glu Phe Tyr Leu Ala Met Pro Phe
1               5                   10                  15

<210> SEQ ID NO 110
<211> LENGTH: 15
<212> TYPE: PRT
<213> ORGANISM: Homo sapiens

<400> SEQUENCE: 110

Arg Leu Leu Glu Phe Tyr Leu Ala Met Pro Phe Ala Thr Pro Met
1               5                   10                  15

<210> SEQ ID NO 111
<211> LENGTH: 15
<212> TYPE: PRT
<213> ORGANISM: Homo sapiens

<400> SEQUENCE: 111

Phe Tyr Leu Ala Met Pro Phe Ala Thr Pro Met Glu Ala Glu Leu
1               5                   10                  15

<210> SEQ ID NO 112
<211> LENGTH: 15
<212> TYPE: PRT
<213> ORGANISM: Homo sapiens

<400> SEQUENCE: 112

Met Pro Phe Ala Thr Pro Met Glu Ala Glu Leu Ala Arg Arg Ser
1               5                   10                  15

<210> SEQ ID NO 113
<211> LENGTH: 13
<212> TYPE: PRT
<213> ORGANISM: Homo sapiens

<400> SEQUENCE: 113

Thr Pro Met Glu Ala Glu Leu Ala Arg Arg Ser Leu Ala
1               5                   10

```
<210> SEQ ID NO 114
<211> LENGTH: 14
<212> TYPE: PRT
<213> ORGANISM: Homo sapiens

<400> SEQUENCE: 114

Met Glu Ala Glu Leu Ala Arg Arg Ser Leu Ala Gln Asp Ala
1               5                   10

<210> SEQ ID NO 115
<211> LENGTH: 14
<212> TYPE: PRT
<213> ORGANISM: Homo sapiens

<400> SEQUENCE: 115

Glu Leu Ala Arg Arg Ser Leu Ala Gln Asp Ala Pro Pro Leu
1               5                   10

<210> SEQ ID NO 116
<211> LENGTH: 15
<212> TYPE: PRT
<213> ORGANISM: Homo sapiens

<400> SEQUENCE: 116

Arg Arg Ser Leu Ala Gln Asp Ala Pro Pro Leu Pro Val Pro Gly
1               5                   10                  15

<210> SEQ ID NO 117
<211> LENGTH: 15
<212> TYPE: PRT
<213> ORGANISM: Homo sapiens

<400> SEQUENCE: 117

Ala Gln Asp Ala Pro Pro Leu Pro Val Pro Gly Val Leu Leu Lys
1               5                   10                  15

<210> SEQ ID NO 118
<211> LENGTH: 15
<212> TYPE: PRT
<213> ORGANISM: Homo sapiens

<400> SEQUENCE: 118

Pro Pro Leu Pro Val Pro Gly Val Leu Leu Lys Glu Phe Thr Val
1               5                   10                  15

<210> SEQ ID NO 119
<211> LENGTH: 15
<212> TYPE: PRT
<213> ORGANISM: Homo sapiens

<400> SEQUENCE: 119

Val Pro Gly Val Leu Leu Lys Glu Phe Thr Val Ser Gly Asn Ile
1               5                   10                  15

<210> SEQ ID NO 120
<211> LENGTH: 15
<212> TYPE: PRT
<213> ORGANISM: Homo sapiens

<400> SEQUENCE: 120

Leu Leu Lys Glu Phe Thr Val Ser Gly Asn Ile Leu Thr Ile Arg
1               5                   10                  15
```

<210> SEQ ID NO 121
<211> LENGTH: 15
<212> TYPE: PRT
<213> ORGANISM: Homo sapiens

<400> SEQUENCE: 121

Phe Thr Val Ser Gly Asn Ile Leu Thr Ile Arg Leu Thr Ala Ala
1               5                   10                  15

<210> SEQ ID NO 122
<211> LENGTH: 14
<212> TYPE: PRT
<213> ORGANISM: Homo sapiens

<400> SEQUENCE: 122

Gly Asn Ile Leu Thr Ile Arg Leu Thr Ala Ala Asp His Arg
1               5                   10

<210> SEQ ID NO 123
<211> LENGTH: 15
<212> TYPE: PRT
<213> ORGANISM: Homo sapiens

<400> SEQUENCE: 123

Leu Thr Ile Arg Leu Thr Ala Ala Asp His Arg Gln Leu Gln Leu
1               5                   10                  15

<210> SEQ ID NO 124
<211> LENGTH: 15
<212> TYPE: PRT
<213> ORGANISM: Homo sapiens

<400> SEQUENCE: 124

Leu Thr Ala Ala Asp His Arg Gln Leu Gln Leu Ser Ile Ser Ser
1               5                   10                  15

<210> SEQ ID NO 125
<211> LENGTH: 13
<212> TYPE: PRT
<213> ORGANISM: Homo sapiens

<400> SEQUENCE: 125

Asp His Arg Gln Leu Gln Leu Ser Ile Ser Ser Cys Leu
1               5                   10

<210> SEQ ID NO 126
<211> LENGTH: 15
<212> TYPE: PRT
<213> ORGANISM: Homo sapiens

<400> SEQUENCE: 126

Arg Gln Leu Gln Leu Ser Ile Ser Ser Cys Leu Gln Gln Leu Ser
1               5                   10                  15

<210> SEQ ID NO 127
<211> LENGTH: 15
<212> TYPE: PRT
<213> ORGANISM: Homo sapiens

<400> SEQUENCE: 127

Leu Ser Ile Ser Ser Cys Leu Gln Gln Leu Ser Leu Leu Met Trp
1               5                   10                  15

<210> SEQ ID NO 128
<211> LENGTH: 12

```
<212> TYPE: PRT
<213> ORGANISM: Homo sapiens

<400> SEQUENCE: 128

Ser Cys Leu Gln Gln Leu Ser Leu Leu Met Trp Ile
1               5                   10

<210> SEQ ID NO 129
<211> LENGTH: 14
<212> TYPE: PRT
<213> ORGANISM: Homo sapiens

<400> SEQUENCE: 129

Leu Gln Gln Leu Ser Leu Leu Met Trp Ile Thr Gln Cys Phe
1               5                   10

<210> SEQ ID NO 130
<211> LENGTH: 15
<212> TYPE: PRT
<213> ORGANISM: Homo sapiens

<400> SEQUENCE: 130

Leu Ser Leu Leu Met Trp Ile Thr Gln Cys Phe Leu Pro Val Phe
1               5                   10                  15

<210> SEQ ID NO 131
<211> LENGTH: 13
<212> TYPE: PRT
<213> ORGANISM: Homo sapiens

<400> SEQUENCE: 131

Met Trp Ile Thr Gln Cys Phe Leu Pro Val Phe Leu Ala
1               5                   10

<210> SEQ ID NO 132
<211> LENGTH: 15
<212> TYPE: PRT
<213> ORGANISM: Homo sapiens

<400> SEQUENCE: 132

Ile Thr Gln Cys Phe Leu Pro Val Phe Leu Ala Gln Pro Pro Ser
1               5                   10                  15

<210> SEQ ID NO 133
<211> LENGTH: 15
<212> TYPE: PRT
<213> ORGANISM: Homo sapiens

<400> SEQUENCE: 133

Phe Leu Pro Val Phe Leu Ala Gln Pro Pro Ser Gly Gln Arg Arg
1               5                   10                  15

<210> SEQ ID NO 134
<211> LENGTH: 321
<212> TYPE: PRT
<213> ORGANISM: Homo sapiens

<400> SEQUENCE: 134

His Ser Ala Arg Met Tyr Asn Met Met Glu Thr Glu Leu Lys Pro Pro
1               5                   10                  15

Gly Pro Gln Gln Thr Ser Gly Gly Gly Gly Asn Ser Thr Ala Ala
                20                  25                  30

Ala Ala Gly Gly Asn Gln Lys Asn Ser Pro Asp Arg Val Lys Arg Pro
            35                  40                  45
```

```
Met Asn Ala Phe Met Val Trp Ser Arg Gly Gln Arg Lys Met Ala
        50                  55                  60
Gln Glu Asn Pro Lys Met His Asn Ser Glu Ile Ser Lys Arg Leu Gly
65                  70                  75                  80
Ala Glu Trp Lys Leu Leu Ser Glu Thr Glu Lys Arg Pro Phe Ile Asp
                85                  90                  95
Glu Ala Lys Arg Leu Arg Ala Leu His Met Lys Glu His Pro Asp Tyr
                100                 105                 110
Lys Tyr Arg Pro Arg Arg Lys Thr Lys Thr Leu Met Lys Lys Asp Lys
        115                 120                 125
Tyr Thr Leu Pro Gly Gly Leu Leu Ala Pro Gly Gly Asn Ser Met Ala
        130                 135                 140
Ser Gly Val Gly Val Gly Ala Gly Leu Gly Ala Gly Val Asn Gln Arg
145                 150                 155                 160
Met Asp Ser Tyr Ala His Met Asn Gly Trp Ser Asn Gly Ser Tyr Ser
                165                 170                 175
Met Met Gln Asp Gln Leu Gly Tyr Pro Gln His Pro Gly Leu Asn Ala
                180                 185                 190
His Gly Ala Ala Gln Met Gln Pro Met His Arg Tyr Asp Val Ser Ala
                195                 200                 205
Leu Gln Tyr Asn Ser Met Thr Ser Ser Gln Thr Tyr Met Asn Gly Ser
        210                 215                 220
Pro Thr Tyr Ser Met Ser Tyr Ser Gln Gln Gly Thr Pro Gly Met Ala
225                 230                 235                 240
Leu Gly Ser Met Gly Ser Val Val Lys Ser Glu Ala Ser Ser Ser Pro
                245                 250                 255
Pro Val Val Thr Ser Ser Ser His Ser Arg Ala Pro Cys Gln Ala Gly
                260                 265                 270
Asp Leu Arg Asp Met Ile Ser Met Tyr Leu Pro Gly Ala Glu Val Pro
        275                 280                 285
Glu Pro Ala Ala Pro Ser Arg Leu His Met Ser Gln His Tyr Gln Ser
        290                 295                 300
Gly Pro Val Pro Gly Thr Ala Ile Asn Gly Thr Leu Pro Leu Ser His
305                 310                 315                 320
Met
```

IMMUNE BIOMARKERS AND ASSAYS PREDICTIVE OF CLINICAL RESPONSE TO IMMUNOTHERAPY FOR CANCER

CROSS-REFERENCE TO RELATED APPLICATION

This application is a 35 U.S.C. §371 national phase application of, and claims priority to, PCT Application No. PCT/US2013/029951, filed Mar. 8, 2013, which claims priority under 35 U.S.C. §119(e) to U.S. Provisional Application Ser. No. 61/646,541, filed May 14, 2012, the contents of all of which are incorporated by reference herein in their entireties.

STATEMENT REGARDING FEDERALLY SPONSORED RESEARCH OR DEVELOPMENT

This invention was made with government support under CA135110 and A1079222 awarded by National Institutes of Health. The government has certain rights in the invention.

BACKGROUND OF THE INVENTION

Non-small cell lung cancer (NSCLC) is the leading cause of cancer-related mortality in the U.S. with over 200,000 new cases in 2011 and estimated 5-year survival of only 15%. Although lung cancer was initially thought to be non-immunogenic, several lines of evidence now support harnessing the properties of the immune system to resist this cancer. Endogenous anti-tumor T cell responses delay malignant tumor progression in mouse models of lung adenocarcinoma (DuPage et al., 2011, Cancer Cell 19(1): 72-85). Properties and distribution of infiltrating T cells has been linked to improved survival in NSCLC (Suzuki et al., 2011, Clin Cancer Res 17(16):5247-56; Ruffini et al., 2009, Ann Thorac Surg, 87(2):365-71). Recent studies with antibodies blocking negative regulators of T cell activation, termed T checkpoint blockade, have shown promising clinical activity in this tumor (Lynch et al., 2012, J Clin Oncol, 30(17):2046-54; Topalian et al., 2012, N Engl J Med, 366(26):2443-54). In particular, antibody mediated blockade of programmed death1 (PD1) recently led to objective tumor regression in 18% of patients with advanced NSCLC (Topalian et al., 2012, N Engl J Med, 366(26):2443-54).

Preclinical studies have shown that the anti-tumor effects of checkpoint blockade depend on underlying immunogenicity of tumors as well as the nature of target antigens. Immune mechanisms underlying responses to these agents may depend on the specific tumor type and the clinical setting such as prophylaxis or therapy (van Elsas et al., 2001, J Exp Med, 194(4):481-9). Although several antigenic targets have been identified in NSCLC, the nature of antigens that correlate with protective immunity in lung cancer remain unknown. Protective immunity may depend on targets critical for biology of the specific cancer. However, many of the antigens studied to date in lung cancer have not been shown to be critical for tumorigenicity.

SOX2 is a transcription factor shown to be critical for pluripotency and stemness in human embryonal stem cells and linked to their tumorigenicity (Takahashi et al., 2007, Cell, 131(5):861-72; Boyer et al., 2005, Cell, 122(6):947-56). Several studies have suggested an important role for SOX2 in the pathogenesis of lung cancer. SOX2 was identified as a common target of genomic amplification and a lineage survival oncogene in squamous cell cancers (Bass et al., 2009, Nat Genet, 41(11):1238-42; Hussenet & Manoir, 2010, Cell Cycle, 9(8):Epub; Yuan et al., 2010, PLoS One, 5(2):e9112; Lu et al., 2011, PLoS One, 5(6):e11022). Genomic abnormalities in SOX2 are also detected in pre-neoplastic lesions in the lung, implying it as a potential driver oncogene (McCaughan et al., 2010, Am J Respir Crit Care Med, 182(1):83-91). SOX2 has been implicated in the context of stem cells in lung tissue and cancer stem cells in adenocarcinoma of the lung (Kim et al., 2005, Cell, 121(6): 823-35; Leung et al., 2011, PLoS One, 5(11):e14062; Tompkins et al., 2009, PLoS One, 4(12):e8248; Nakatsugawa et al., 2011, Lab Invest, 91(12):1796-804; Xiang et al., 2011, Br J Cancer, 104(9):1410-7). SOX2 was also shown to regulate oncogenic networks and tumorigenicity in diverse types of lung cancer (Chen et al., 2012, PLoS One, 7(5): e36326). While SOX2 and other pluripotency genes have not yet proven to be easily druggable, the capacity of the immune system to target these genes has been shown (Spisek et al., 2007, J Exp Med, 204(4):831-40; Dhodapkar et al., 2010, Proc Natl Acad Sci USA, 107(19):8718-23; Dhodapkar & Dhodapkar, 2011, Cancer J, 17(5):397-402; Dhodapkar, 2010, Curr Opin Immunol, 22(2):245-50).

Several studies have analyzed the presence of antibody responses to SOX2 in patients with lung cancer, and the presence of these antibodies has been particularly associated with small cell lung cancer (SCLC) (Gure et al., 2000, Proc Natl Acad Sci USA, 97(8):4198-203; Gnjatic et al., 2009, J Immunol Methods, 341(1-2):50-8; Titulaer et al., 2009, J Clin Oncol, 27(26):4260-7). It has been shown that the presence of naturally occurring T cell immunity to SOX2 was associated with improved survival and reduced risk of clinical malignancy in patients with monoclonal gammopathies (Spisek et al., 2007, J Exp Med, 204(4):831-40). However, the nature of T cell immunity to this antigen in lung cancer has not yet been described.

Thus, there is an unmet need in the art for biomarkers and assays for identifying patients more likely to benefit from immunotherapy for cancer. The present invention addresses this unmet need in the art.

BRIEF SUMMARY OF THE INVENTION

The invention relates to discovery that the presence of an immune response directed against SOX2 in a subject correlates positively with an anti-tumor response in the subject following immunotherapy. In one embodiment, the invention a method of determining whether a subject with cancer is a candidate for immunotherapy for the cancer including the steps of subjecting a subject's biological sample to at least one assay to detect the presence or absence of at least one biomarker of an immune response directed against a component of a cancer cell of the subject, wherein when at least one biomarker of an immune response directed against the component of the cancer cell of the subject is detected, the subject is identified as a candidate for immunotherapy for cancer, and wherein when at least one biomarker of an immune response directed against the component of the cancer cell of the subject is not detected, the subject is identified as not being a candidate for immunotherapy. In some embodiments, where the subject is identified as a candidate for immunotherapy for cancer, the subject is administered an immunotherapy for cancer. In other embodiments, where the subject is identified as not being a candidate for immunotherapy for cancer, the subject is excluded from receiving an immunotherapy for cancer.

In another embodiment, the invention is a kit for determining whether a subject with cancer is a candidate for immunotherapy for the cancer including a container for containing a biological sample derived from the subject, at least one assay for detecting the presence or absence of at least one biomarker of an immune response directed against a component of a cancer cell of the subject, instructional material for performing the at least one assay, wherein when at least one biomarker of an immune response directed against the component of the cancer cell of the subject is detected, the subject is identified as a candidate for immunotherapy for cancer, and wherein when at least one biomarker of an immune response directed against the component of the cancer cell of the subject is not detected, the subject is identified as not being a candidate for immunotherapy.

In one embodiment, the component of the cancer cell is SOX2 or a fragment thereof. In some embodiments, the SOX2 comprises the amino acid sequence of SEQ ID NO: 134. In some embodiments, the SOX2 fragment is at least one peptide comprising an amino acid sequence selected from the group consisting of SEQ ID NOs: 1-86.

In some embodiments, the assay is at least one of an immune cell proliferation assay, an assay for detecting immune effector molecule production by immune cells, or an assay for measuring immune effector molecule production by immune cells. In other embodiments, the assay is at least one of flow cytometry, immunocytochemistry, immunohistochemistry, ELISPOT, ELISA or variations thereof.

In some embodiments, the at least one biomarker of an immune response directed against a component of the cancer cell of the subject is at least one biomarker of a cell-mediated immune response. In other embodiments, the cell-mediated immune response is a T cell response. In some embodiments, the at least one biomarker of an immune response directed against a component of the cancer cell of the subject is T cell proliferation in response to stimulation with the component of the cancer cell of the subject. In some embodiments, the at least one biomarker of an immune response directed against a component of the cancer cell of the subject is an immune cell producing at least one type of immune effector molecule in response to stimulation with the component of the cancer cell of the subject. In some embodiments, the at least one biomarker of an immune response directed against a component of the cancer cell of the subject is at least one immune effector molecule selected from the group consisting of IFN-γ, IP10, IL-2, IL-4, IL-10, IL-12, and TNF-α.

In other embodiments, the at least one biomarker of an immune response directed against a component of the cancer cell of the subject is at least one biomarker of a humoral immune response. In some embodiments, the at least one biomarker of an immune response directed against a component of the cancer cell of the subject is at least one antibody that specifically binds the component of the cancer cell of the subject.

In some embodiments, the at least one biomarker of an immune response directed against the component of the cancer cell of the subject is detected and the level of the at least one biomarker detected is quantified. In some embodiments, the at least one biomarker of an immune response directed against a component of the cancer cell of the subject is detected and the level of the at least one biomarker detected is quantified and the level of the least one biomarker is compared with the level of at least one comparator selected from the group consisting of a negative control, a normal control, a positive control, a historical control and a historical norm. In some embodiments, the level of the at least one biomarker of an immune response directed against a component of the cancer cell of the subject differs from the level of the comparator by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, or by at least 500%.

In various embodiments, the biological sample is at least one selected from the group consisting of blood, serum, plasma, lymph and tumor tissue. In some embodiments, the biological sample comprises at least one type of cells selected from the group consisting of peripheral blood lymphocytes, peripheral blood mononuclear cells, B cells and T cells. In other embodiments, the biological sample comprises at least one antibody. In some embodiments, the biological sample comprises at least one antibody that specifically binds to the component of the cancer cell of the subject. In some embodiments, the biological sample comprises at least one immune effector molecule. In some embodiments, the biological sample comprises at least one immune effector molecule selected from the group consisting of IFN-γ, IP10, IL-2, IL-4, IL-10, IL-12, and TNF-α.

In some embodiments, the cancer is SOX2+ cancer. In some embodiments, the cancer is lung cancer. In some embodiments, the cancer is non-small cell lung cancer (NSCLC). In some embodiments, the at least one biomarker of an immune response directed against a component of the cancer cell of the subject is detected using a molecule that specifically binds to the biomarker or a fragment thereof. In some embodiments, the molecule is selected from the group consisting of an antibody and a fragment of an antibody.

In some embodiments, the immunotherapy is a PD1 blockade immunotherapy. In some embodiments, the PD1 blockade immunotherapy comprises the administration of at least one selected from the group consisting of AMP224, BMS936558, GSK2661380, 0N04538, CT011, MK3475, MEDI4736, BMS936559, RG7446, MPDL3280A and MDX1105.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A: Representative patient with SOX2 reactivity. FIG. 1B: Representative patient without SOX2 reactivity. FIG. 1C: PBMCs obtained from patients with advanced NSCLC were tested for the presence of T cell reactivity against SOX2 (n=35) and NY-ESO1 (n=23) using overlapping peptides from the proteins as in FIG. 1A. FIG. 1C shows the percentage of patients with detectable immunity to SOX2 (60%) or NY-ESO1 (74%). FIG. 1D: PBMCS from lung cancer patients were labeled with CFSE cell tracker dye and co-cultured with peptide library from SOX2 protein (5 µg/ml) in the presence of anti-CD28 and anti- CD49D (1 μg/ml of each) for 7 days. Proliferation of T cells in response to SOX2 was determined using flow cytometry. FIG. 1E: The overlapping peptide library from SOX2 protein was divided into 4 mixes consisting of consecutive peptides: Mix1 amino acids (aa) 1-89; Mix2 aa 79-171; Mix3 aa 161-246; Mix4 aa 236-321. FIG. 1E shows the reactivity of the SOX2-positive patients to the different regions of the SOX2 protein. The total percentage exceeds 100 as some patients have reactivity against more than one region of the protein. FIG. 1F: PBMCs from patients with lung cancer were examined for the presence of SOX2-reactive T cells by luminex assay as above. FIG. 1F shows T cell reactivity to SOX2 in lung cancer patients, those with squamous cell carcinoma (SQ) and those with non-squamous cell carcinoma (NS). FIG. 1G: PBMCs were incubated with individual peptides from SOX2 MIX2 for 48 hours and tested for the presence of IP10 using luminex assay. FIG. 1G shows individual peptide reactivity for 2 different patients. FIG. 1H: Plasma obtained from patients was tested for the presence of antibodies against SOX2 protein as well as EBV nuclear antigen using ELISA. FIG. 1H shows the percent of patients with antibodies against SOX2 (7 of 25; 28%) and EBNA1 (22 of 25; 88%).

FIG. 2A shows clinical response to anti-PD1 defined as response ≥PR in patients who have T cells reactive against SOX2 (POS) as well as those who lack T cells reactive against SOX2 (NEG). FIG. 2B shows T cells reactivity against viral antigen mix CEF (peptide mix from CMV, EBV and Influenza) in patients who had a clinical response (≥PR) to anti-PD1 therapy (YES) versus those who did respond to therapy (NO). FIG. 2C: shows clinical response (≥PR) to anti-PD1 therapy in patients with NYESO1 reactive T cells (POS) as well as those who lacking these responses (NEG). FIG. 2D: shows clinical response to anti-PD1 therapy in patients with antibodies (POS) or without antibodies (NEG) specifically binding to SOX2 or to EBNA. FIG. 2E: Representative figure from one patient showing T cell reactivity against different regions (Mix1, Mix2, Mix3 and Mix4) of the SOX2 protein before, and 9 months after therapy with anti-PD1. Note increasing number of reactive regions post-therapy. FIG. 2F shows the duration for which patients were able to receive anti-PD1 therapy among patients with detectable SOX2-reactive T cells (POS) versus those lacking these responses (NEG). The circles represent individual patients and the bar represents the mean for the group.

FIGS. 3A-3D shows SOX2 expression in 2 representative patients showing expression of SOX2 in both squamous and non-squamous histologies. While the expression of SOX2 is greater in squamous cell cancer, SOX2-expressing cells are also detected in non-squamous histology.

DETAILED DESCRIPTION

Figure 1A:
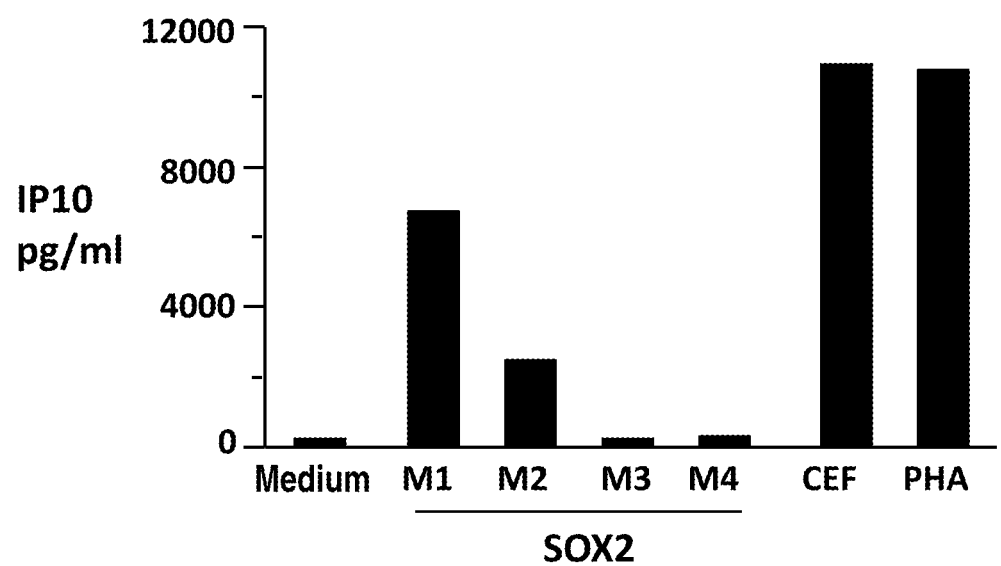
FIGS. 1A-1H depict the results of experiments evaluating antigen-specific T cell and humoral responses in non-small cell lung cancer. Peripheral blood mononuclear cells were co-cultured with medium alone, overlapping peptides from SOX2 protein (3 mcg/ml, Mix1, Mix2, Mix3 and Mix4), peptide pool derived from viral antigens (CEF) or PHA. After 48 hours, the cell supernatant was harvested and examined for the presence of Interferon γ-Induced Protein 10 (IP10).

The present invention relates to discovery that the presence of an immune response directed against SOX2 correlates positively with tumor regression following immunotherapy. Thus, the compositions and methods of the present invention relate to predictors of a subject's responsiveness to immunotherapy for cancer. In some embodiments, the cancer is SOX2+ cancer. In some embodiments, the cancer is lung cancer. In some embodiments, the cancer is non-small cell lung cancer (NSCLC). In particular embodiments, the cancer is SOX2+ NSCLC. As described herein, immunity directed against SOX2 is detectable in a significant number of patients with SOX2+ cancer, including NSCLC. Further, a correlation between an immune response directed against SOX2+ and tumor regression following immunotherapy is described herein. In some embodiments, the immunotherapy is a blockade of known immune checkpoint, such as CTLA4 or PD1. In some embodiments, the immunotherapy is a PD1 blockade. Accordingly, the present invention relates to the detection of an immune response directed against SOX2 in a subject with cancer as a biomarker for the success of immunotherapy in a subject with cancer.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, etc.) from those organisms, tissues, cells or components thereof that display the "normal" (expected) respective characteristic. Characteristics which are normal or expected for one cell or tissue type, might be abnormal for a different cell or tissue type.

The term "cancer" as used herein is defined as disease characterized by the aberrant proliferation and/or growth of cells. Cancer cells can spread locally or through the bloodstream and lymphatic system to other parts of the body. Examples of various cancers amenable to the invention include, but are not limited to, breast cancer, prostate cancer, ovarian cancer, cervical cancer, skin cancer, pancreatic cancer, colorectal cancer, renal cancer, liver cancer, bone cancer, brain cancer, lymphoma, leukemia, lung cancer, and the like.

"Complementary" as used herein refers to the broad concept of subunit sequence complementarity between two nucleic acids. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

As used herein "endogenous" refers to any material from or produced inside an organism, cell, tissue or system.

The term "expression" as used herein is defined as the transcription and/or translation of a particular nucleotide sequence.

"Fragment" as the term is used herein, is a nucleic acid or polypeptide that differs in length (i.e., in the number of nucleotides or amino acids) from the length of a reference nucleic acid or polypeptide, but retains essential properties of the reference molecule. Preferably, the fragment is at least about 50% of the length of the reference molecule. More preferably, the fragment is at least about 75% of the length of the reference molecule. Even more preferably, the fragment is at least about 95% of the length of the reference molecule.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity."

As used herein, "hybridization," "hybridize(s)" or "capable of hybridizing" is understood to mean the forming of a double or triple stranded molecule or a molecule with partial double or triple stranded nature. Complementary sequences in the nucleic acids pair with each other to form a double helix. The resulting double-stranded nucleic acid is a "hybrid." Hybridization may be between, for example two complementary or partially complementary sequences. The hybrid may have double-stranded regions and single stranded regions. The hybrid may be, for example, DNA: DNA, RNA:DNA or DNA:RNA. Hybrids may also be formed between modified nucleic acids (e.g., LNA compounds). One or both of the nucleic acids may be immobilized on a solid support. Hybridization techniques may be used to detect and isolate specific sequences, measure homology, or define other characteristics of one or both strands. The stability of a hybrid depends on a variety of factors including the length of complementarity, the presence of mismatches within the complementary region, the temperature and the concentration of salt in the reaction or nucleotide modifications in one of the two strands of the hybrid.

The term "inhibit," as used herein, means to suppress or block an activity or function by at least about ten percent relative to a control value. Preferably, the activity is suppressed or blocked by 50% compared to a control value, more preferably by 75%, and even more preferably by 95%.

As used herein, an "instructional material" includes a publication, a recording, a diagram, or any other medium of expression which can be used to communicate the usefulness of a compound, composition, assay or method of the invention in a kit for detecting or measuring immune biomarkers predictive of the clinical response to immunotherapy for cancer. The instructional material of the kit of the invention can, for example, be affixed to a container which contains the identified compound, composition, assay, or methods of the invention or be shipped together with a container which contains the identified compound, composition, assay, or method. Alternatively, the instructional material can be shipped separately from the container with the intention that the instructional material and the compound, composition, assay, or method be used cooperatively by the recipient.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant," as used herein, refers to either a nucleic acid or protein comprising a mutation.

"Naturally occurring" as used herein describes a composition that can be found in nature as distinct from being artificially produced. For example, a nucleotide sequence present in an organism, which can be isolated from a source in nature and which has not been intentionally modified by a person, is naturally occurring.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand." Sequences on the DNA strand which are located 5' to a reference point on the DNA are referred to as "upstream sequences." Sequences on the DNA strand which are 3' to a reference point on the DNA are referred to as "downstream sequences."

As used herein, "polynucleotide" includes cDNA, RNA, DNA/RNA hybrid, antisense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

The term "recombinant DNA" as used herein is defined as DNA produced by joining pieces of DNA from different sources.

The term "recombinant polypeptide" as used herein is defined as a polypeptide produced by using recombinant DNA methods.

The phrase "response to immunotherapy" refers to the clinical benefit imparted to a patient suffering from cancer (such as a cancer where some, or all, of the cancer cells express SOX2 (i.e., SOX2+)) upon administration of an immunotherapy. A clinical benefit includes a reduction in the frequency or severity of at least one sign or symptom experienced by the patient, a complete remission, a partial remission, a stable disease (without progression), progression-free survival, disease free survival, improvement in the time-to-progression (of the disease), improvement in the time-to-death, or improvement in the overall survival time of the patient from or as a result of the treatment with the HER dimerization inhibitor. There are criteria for determining a response to therapy and those criteria allow comparisons of the efficacy to alternative treatments (Slapak and Kufe, Principles of Cancer Therapy, in Harrisons's Principles of Internal Medicine, 13th edition, eds. Isselbacher et al., McGraw-Hill, Inc., 1994). For example, a complete response or complete remission of cancer is the disappearance of all detectable malignant disease. A partial response or partial remission of cancer may be, for example, an approximately 50 percent decrease in the product of the greatest perpendicular diameters of one or more lesions or where there is not an increase in the size of any lesion or the appearance of new lesions.

As used herein, the term "progression of cancer" includes and may refer to metastasis; a recurrence of cancer, or an at least approximately 25 percent increase in the size of one lesion, or the appearance of new lesions. The progression of cancer, such as SOX2+ cancer, is "inhibited" if progression, recurrence or metastasis of the cancer is reduced, slowed, delayed, or prevented.

As used herein, the term "marker" or "biomarker" is meant to include a parameter which is useful according to this invention for determining the presence and/or magnitude of an immune response directed against cancer, such as SOX2+ cancer.

The level of a marker or biomarker "significantly" differs from the level of the marker or biomarker in a reference sample if the level of the marker in a sample from the patient differs from the level in a sample from the reference subject by an amount greater than the standard error of the assay employed to assess the marker, and preferably at least 10%, and more preferably 25%, 50%, 75%, 100%, 125%, 150%, 175%, 200%, 300%, 400%, 500% or 1,000% of that amount.

The term "SOX2" refers to the SRY (sex determining region Y)-box 2 gene that encodes a protein and to the protein itself that is a member of the family of Sox family of transcription factors.

"Sample" or "biological sample" as used herein means a biological material from a subject, including but is not limited to organ, tissue, cell, exosome, blood, plasma, urine and other body fluid. A sample can be any source of material obtained from a subject.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

"Synthetic mutant" includes any purposefully generated mutant or variant protein or nucleic acid. Such mutants can be generated by, for example, chemical mutagenesis, polymerase chain reaction (PCR) based approaches, or primer-based mutagenesis strategies well known to those skilled in the art.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by the invention include, but are not restricted to, oligonucleotides, nucleic acids, antibodies, cell membrane receptors, cell surface molecules, monoclonal antibodies and antisera reactive with specific antigenic determinants (such as on viruses, cells or other materials), drugs, peptides, cofactors, lectins, sugars, polysaccharides, cells, cellular membranes, and organelles. Targets are sometimes referred to in the art as anti-probes.

"Variant" as the term is used herein, is a nucleic acid sequence or a polypeptide sequence that differs in sequence from a reference nucleic acid sequence or polypeptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of polypeptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to predictors of a subject's responsiveness to immunotherapy of cancer. In some embodiments, the cancer is SOX2+ cancer. As used herein, a SOX2+ cancer is a cancer where some, or all, of the subject's cancer cells express SOX2. In some embodiments, the cancer is lung cancer. In some embodiments, the cancer is non-small cell lung cancer (NSCLC). In particular embodiments, the cancer is SOX2+ NSCLC. As described herein, immunity directed against SOX2 is detectable in a significant number of patients with SOX2+ cancer, including NSCLC. Further, a correlation between an immune response directed against SOX2+ and tumor regression following immunotherapy is described herein. In some embodiments, the immunotherapy is a blockade of an immune checkpoint, such as CTLA4 or PD1. In some embodiments, the immunotherapy is a PD1 blockade. Accordingly, the present invention relates to the detection of an immune response directed against SOX2 in a subject with cancer as a biomarker of the success of immunotherapy in the subject with cancer.

Some individuals who develop cancer develop an immune response directed against one or more components of their cancer cells. In one embodiment, the invention includes a method of detecting an immune response directed against a component of a subject's cancer cells, for use as a biomarker of the success of administering immunotherapy to that subject. In one embodiment, the invention includes a method of detecting an immune response directed against SOX2, for use as a biomarker of the success of administering immunotherapy to that subject. In some embodiments, the cancer is lung cancer. In some embodiments, the cancer is non-small cell lung cancer (NSCLC). In particular embodiments, the cancer is SOX2+ NSCLC.

In one embodiment, the invention includes a method of detecting and/or measuring an immune response directed against an antigen, such as SOX2 or a fragment thereof. In various embodiments, the SOX2 fragment of the invention comprises at least one SOX2 fragment comprising an amino acid sequence of at least one of SEQ ID NOs: 1-86. In one embodiment, the method of detecting or measuring an immune response directed against an antigen, such as SOX2 or a fragment thereof, includes isolating whole blood, or specifically peripheral blood mononuclear cells (PBMCs), from a subject and contacting the blood or PBMCs with SOX2 at least one SOX2 fragment comprising an amino acid sequence of at least one of SEQ ID NOs: 1-86 to determine the absence, presence or magnitude of an immune response directed against SOX2 or a fragment thereof. Detection of an immune response directed against the SOX2 or a fragment thereof is an indication that the subject has developed immunity against SOX2 or a fragment thereof. In various embodiments, the immune response directed against SOX2 or a fragment thereof, is a cell-mediated immune response, a humoral immune response, or both.

In some embodiments, the detection of a cellular immune response can be accomplished by detecting T cells, or T cell responses, specific for an antigen, such as SOX2 or fragment thereof. In one embodiment, the T cells are in the form of peripheral blood lymphocytes (PBLs). In another embodiment, the T cells are in the form of peripheral blood mononuclear cells (PBMCs). PBLs are mature lymphocytes that are found circulating in the blood, as opposed to being located in organs such as lymph nodes, spleen, thymus, liver or bone marrow. In some embodiments, T cells are isolated from body fluids or tissue collected from lymph nodes, spleen, thymus, liver or bone marrow. In other embodiments, T cells are isolated from tissue in or near tumors. However, it will be understood that any body fluid or tissue containing T cells can be used in the methods of the current invention, which are not restricted to T cells from disease sites or from blood.

In one embodiment, the assay according to the invention is performed on PBMCs obtained from a subject. The diagnostic assay of the invention is performed using a diagnostic kit comprising at least one test antigen, such as SOX2 or at least one fragment thereof. Non-limiting examples of SOX2 fragments useful in the invention include SEQ ID NOs:1-86, and any combination thereof. For example, PBMCs are isolated from a subject and the isolated PBMCs are contacted with one or more of the antigens of the invention in order to determine the reactivity of the PBMCs against the antigen. The number of PBMCs secreting one or more types of immune effector molecules in response to stimulation with a test antigen, such as SOX2 or a fragment thereof, can be measured to detect, measure or quantify the immune response to the test antigen.

PBMCs from patients or subjects needing assessment for an immune response directed against SOX2 may be used to detect, measure or quantify the immune response directed against SOX2. Generally, the PBMCs from test subjects or mammals are isolated and then cultured with one or more SOX2 polypeptides, peptide pools or select peptides from the polypeptide, or nucleic acids (DNA or RNA and their derivatives) encoding the polypeptide, of the invention. After a period of time, cell culture supernatants are collected and immune effector molecule production by the PBMCs is measured. In one embodiment, the amount of immune effector molecule secreted by the PBMCs is compared to a control PBMC sample (e.g., from a subject known not to have an immune response against the antigen). A greater or lesser amount of a particular immune effector molecule present in the test sample is indicative of an immune directed against that antigen. Similar assays are described in more detail in Dillon, et al., J. of Clinical Microbiol. 38:3285-3290 (2000) and in U.S. Pat. No. 7,387,882. Immune effector molecules which can be measured in the PBMC assay described above include but are not limited to any cytokine which the PBMCs can produce (e.g., IFN-gamma, IPO, IL-12, IL-5, and IL-2).

T cells, NK cells, B cells and macrophages derived from SOX2+ cancer patients can be prepared using methods known to those of ordinary skill in the art. The selection of cell type for use in evaluating an immune response to an antigen, such as SOX2 or a fragment thereof, will vary depending on the type of immune response sought to be detected. By way of non-limiting example, the detection of IL-12 production may be most readily evaluated using preparations containing B-cells and/or macrophages. For example, a preparation of PBMCs (i.e., peripheral blood mononuclear cells) can be employed without further separation of component cells. PBMCs can generally be prepared, for example, using density centrifugation through Ficoll (Winthrop Laboratories, NY). T cells for use in the assays described herein can also be purified directly from PBMCs. Alternatively, an enriched T cell line reactive against SOX2 or a fragment thereof, or T cell clones reactive to individual SOX2 fragments, can be employed. Such T cell clones can be generated by, for example, culturing PBMCs from SOX2+ cancer patients with SOX2 or fragments thereof for an extended period (e.g., 1-4 weeks). This allows expansion of only the SOX2-specific T cells, resulting in a line composed entirely, or nearly entirely, of such cells. These cells can then be cloned and tested with individual proteins, using methods known to those of ordinary skill in the art, to more accurately define individual T cell specificity. In general, antigens that test positive in assays for proliferation and/or cytokine production (i.e., IFN-γ, IP10 and/or IL-12 production) performed using T cells, NK cells, B cells and/or macrophages derived from a SOX2+ cancer patient are considered immunogenic. Such assays can be performed, for example, using the representative procedures described elsewhere herein. Immunogenic portions of such antigens can be identified using similar assays, and can be present within the polypeptides described herein.

The ability of SOX2 or a fragment thereof to stimulate the production of an immune effector molecule, such as IP10, IFN-γ, TNF-α, and/or IL-2, can be evaluated by contacting cells with SOX2 or a fragment thereof and measuring the level of at least one immune effector molecule produced by the cells. In general, the amount of SOX2 or fragment thereof that is sufficient for the evaluation of about $10^5$ cells ranges from about 10 ng/mL to about 100 µg/mL, and preferably is about 10 µg/mL. The SOX2 or fragment thereof can, but need not, be immobilized on a solid support, such as a bead or a biodegradable microsphere, such as those described in U.S. Pat. Nos. 4,897,268 and 5,075,109. The incubation of SOX2 or fragment thereof with the cells is typically performed at 37° C. for about 2-10 days. Following incubation with SOX2 or fragment thereof, the cells and/or supernatant are assayed for the production of at least one immune effector molecule, such as IFN-γ, IP10, TNF-α, and/or IL-2 (or other proteins made in response to specific antigen stimulation), which can be evaluated by methods known to those of ordinary skill in the art, such as an enzyme-linked immunosorbent assay (ELISA) or, a bioassay such as an assay measuring proliferation of T cells.

In one embodiment, the invention includes an assay for measuring the magnitude of a cellular immunologic response to SOX2 or a fragment thereof. In some instances, blood is drawn from a patient and the cells in the blood is contacted with one or more of the SOX2 protein, peptides, peptide pools, select antigenic peptides, or other methods used to provide an antigen for immunologic presentation. After a period of time, the amount of an immune effector molecule, or the number of antigen-responsive PBMCs secreting one or more immune effector molecules, is measured to determine the extent of the immune response directed against SOX2 or a fragment thereof. As used herein, immune effector molecules includes cytokines, chemokines, lymphokines, interleukins, interferons, and other molecules produced by antigen-responsive immune cells. It will be readily apparent to the skilled person that the immune effector molecule can be detected by any suitable technique known in the art, for example, ELISPOT, or intracellular cytokine staining followed by flow cytometry, or cytokine secretion and capture assay, or ELISA, or whole-blood ELISA.

In general, the antigen or antigens of the present invention, such as SOX2 and fragment thereof, are recognized by the subject's adaptive immune system. Preferably, the antigen is recognized by a cell-mediated immune response, although the invention also includes approaches based on the humoral immune system as well. In one embodiment, the antigen of the present invention is at least one polypeptide having an amino acid sequence selected from the group consisting of SEQ ID NOs: 1-86, 134, or any combination thereof.

Cell-mediated immune response assays have been developed and have been used in the clinical setting. Measurement of a cell-mediated immune response is important for immune diagnosis of many infectious, autoimmune diseases, and cancer as a marker for detection of T-cell responses to an antigen. Current methods for detecting cell-mediated immune responses include skin tests measuring both immediate and delayed type hypersensitivity, lymphocyte proliferation assays and measurement of immune effector molecules produced by immune cells cultured with antigen. Most in vitro methods for detecting cell-mediated immune responses involve the collection of lymphocytes from whole blood, contacting these lymphocytes with an antigen for periods from 12 hours to 6 days and then detecting T-cell activity in response to the antigen. Established proliferation assay methods, use the uptake of radioactive isotopes or cell tracking dyes (e.g., CF SE) by dividing T-cells as a marker for cell mediated immune response reactivity. More recently, techniques such as a single cell assay (ELISpot) have been used to detect the number of T-cells producing certain immune effector molecules in response to the antigenic stimulation.

The ability of a polypeptide (e.g., an immunogenic antigen, or a portion or other variant thereof) to induce cell proliferation can be evaluated by contacting the cells (e.g., T cells and/or NK cells) with the polypeptide and measuring the proliferation of the cells. In general, the amount of polypeptide that is sufficient for evaluation of about $10^5$ cells ranges from about 10 ng/mL to about 100 µg/mL and preferably is about 10 µg/mL. The incubation of polypeptide with cells may be performed at 37° C. for about 1-10 days, although protocols vary. Following incubation with SOX, or a fragment thereof, the cells are assayed for a proliferative response, which can be evaluated by methods known to those of ordinary skill in the art, such as exposing cells to a pulse of radiolabeled thymidine and measuring the incorporation of label into cellular DNA. In general, an increase in proliferation of at least about two-fold above background (i.e., the proliferation observed for cells cultured without the antigen) is considered a positive proliferation assay.

The present invention provides a method for measuring cell-mediated immune responses in a subject by incubating a sample from the subject which comprises T-cells, alone or in combination with other cells of the immune system, with an antigen. Production of IFN-gamma, IP10, or another cytokine, chemokine or immune effector molecule is then detected. The presence or level of the immune effector molecule is then indicative of the presence or level of the cell mediated immune responsiveness of the subject.

The present invention also provides an assay of the potential or capacity of a subject to mount a cell-mediated immune response against a particular antigen, such as SOX2 or a fragment thereof. The assay is based on measuring immune effector molecule production by cells of the immune system in response to antigenic stimulation. The immune effector molecules may be detected using ligands such as antibodies that are specific for the immune effector molecules or by measuring the level of expression of nucleic acid (e.g., mRNA) encoding the immune effector molecules. The present invention provides, therefore, a means to determine the presence or absence of a cell mediated immune response in a subject and, in turn, provides a means for predicting the likelihood of success of an immunotherapy administered to that subject. By way of non-limiting example, a subject identified as having a cell-mediated immune response directed against SOX2 is more likely to have a clinical response against SOX2+ cancer upon administration of an immunotherapy.

One aspect of the present invention contemplates a method for measuring a cell mediated immune response in a subject. The method comprises collecting a sample from the subject wherein the sample comprises cells of the immune system which are capable of producing immune effector molecules following exposure to an antigen to which the cells are responsive, contacting the sample with an antigen and then measuring the absence, presence or magnitude of the level of an immune effector molecule wherein the absence, presence or magnitude of the immune effector molecule is indicative of the capacity of the subject to mount a cell-mediated immune response in response to that antigen. In some embodiments, the subject is human.

The immune effector molecules detected or measured in the assays of the invention may be any of a variety of molecules which are produced in response to immune cell activation or stimulation by an antigen. Although an interferon such as IFN-γ is a particularly useful immune effector molecule, others include immune effector molecules such as IP10, IL-2, IL-4, IL-10, IL-12, tumor necrosis factor alpha (TNF-alpha), a colony stimulating factor (CSF) such as granulocyte (G)-CSF or granulocyte macrophage (GM)-CSF, amongst many others including proteins associated with degranulation (CD107a), and proteins associated with lysis (e.g., granzyme, perforin, etc.).

Broadly, two commercially available assay formats exist: enzyme-linked immunospot (ELISpot) and enzyme-linked immunoassay (ELISA). Accordingly, the samples can be added to these, or similar assays, to detect the existence of a T cell response directed against the antigen of the invention. However, the invention is not limited to these assays, but rather, the antigens of the present invention can be used in any assay in the art for detecting or measuring an immune response against SOX2 or fragment thereof.

An SOX2+ cancer patient having an immune response against SOX2 can be identified by virtue of having mounted a T cell response to SOX2 or a fragment thereof. In some embodiments, such subjects can be identified based on a positive intradermal skin test response to SOX2 Purified Protein Derivative (PPD) test.

In addition to cell-mediated immune response assays, the antigens of the invention, such as SOX2 or a fragment thereof, may be used in an assay to detect antibodies present in a biological sample from a subject. For example, the antigens of the invention are used as immunological probes to assess the pattern of humoral immunity driven by the presence of cancer. The samples and antigens of the present invention can be used in a variety of assay formats known to those of ordinary skill in the art for detecting antibodies in a sample, or using an antigen binding agent, such as an antibody, to detect polypeptides in a sample. See, e.g., Harlow and Lane, Antibodies: A Laboratory Manual, Cold Spring Harbor Laboratory, 2001. In one example, the assay involves the use of SOX2, or a fragment thereof, immobilized on a solid support to bind to specifically binding antibodies present in the sample. Non-limiting examples of SOX2 and fragments thereof include SEQ ID NOs: 1-86 and 134. The bound polypeptide or antibody (i.e., the formation of a polypeptide-antibody) may then be detected using a detection reagent that contains reporter functionality. Suitable detection reagents include, but are not limited to antibodies that bind to the antibody/polypeptide complex and free polypeptide labeled with a reporter functionality (e.g., in a semi-competitive assay). Alternatively, a competitive assay may be utilized, in which an antibody that binds to the polypeptide is labeled with reporter functionality and allowed to bind to the immobilized antigen after incubation of the antigen with the sample. The extent to which components of the sample inhibit the binding of the labeled antibody to the polypeptide is indicative of the reactivity of the sample with the immobilized polypeptide. In some embodiments, the reporter functionality includes an enzyme, which is bound to the polypeptide, or to an antigen-binding agent, that will react with an appropriate substrate (e.g., a chromogenic substrate) in such a manner as to produce a chemical moiety which can be detected, for example, by spectrophotometric, fluorimetric, or by visual means. Enzymes which can be used to detectably label the polypeptide, such as SOX2 or fragment thereof, or the polypeptide-antibody complex formed include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter functionality depends upon the nature of the reporter functionality. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

The solid support may be any solid material known to those of ordinary skill in the art to which the polypeptide of the invention, such as SOX2 or fragment thereof, may be attached. For example, the solid support may be a test well in a microtiter plate or a nitrocellulose membrane or any other suitable membrane. Alternatively, the support may be a bead or disc, such as, but not limited to, glass, fiberglass, latex or a plastic material such as polystyrene or polyvinylchloride. The support may also be a magnetic particle or a fiber optic sensor.

The antigenic polypeptide of the invention, such as SOX2 or fragment thereof, may be bound to the solid support using a variety of techniques known to those of ordinary skill in the art, which are amply described in the patent and scientific literature. In the context of the present technology, the term "bound" refers to both noncovalent association, such as adsorption, and covalent attachment (which may be a direct linkage between the polypeptide and functional groups on the support or may be a linkage by way of a bridging or cross-linking agent). The polypeptides of the invention, such as SOX2 or fragment thereof, may also be bound by adsorption to a well in a microtiter plate or to a membrane. In such cases, adsorption may be achieved by contacting the polypeptides of the invention, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide or polypeptide binding agent ranging from about 10 ng to about 1 mg, and about 100 mg, is sufficient to bind an adequate amount of polypeptide or antibody.

In some embodiments, in an EIA or ELISA, the assay is performed by first contacting a polypeptide antigen that has been immobilized on a solid support, commonly the well of a microtiter plate, with a test sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide, such as SOX2 or fragment thereof, is immobilized on the support as described above, the remaining protein binding sites on the support are typically blocked. Any suitable blocking agent known to those of ordinary skill in the art, such as bovine serum albumin or Tween20™ (Sigma Chemical Co., St. Louis, Mo., USA) may be employed. The immobilized polypeptide is then incubated with the sample, and antibody is allowed to bind to the polypeptide. The sample may be diluted with a suitable diluent, such as phosphate-buffered saline (PBS) prior to incubation. In some embodiments, an appropriate contact time (i.e., incubation time) is that period of time that is sufficient to detect the presence of antibody within a test biological sample. In some embodiments, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% (v/v) Tween20™. Detection reagent may then be added to the solid support. An appropriate detection reagent is any compound that binds to the immobilized antibody-polypeptide complex and that can be detected by any of a variety of means known to those in the art. Suitable detection reagents include, but are not limited to binding agents such as, Protein A, Protein C, immunoglobulin, lectin or free antigen conjugated to a reporter group. Suitable reported groups include, but are not limited to, e.g., enzymes (such as horseradish peroxidase and alkaline phosphatase), substrates, cofactors, inhibitors, dyes, radionuclides, luminescent groups, fluorescent groups, biotin and colloidal particles, such as colloidal gold and selenium. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., USA, and Pierce, Rockford, Ill., USA).

Of course, numerous other assay formats and protocols exist that are suitable for use in the methods of the present invention. The descriptions are intended to be illustrative only and in no way is considered to limit the invention.

All known variants of ELISA type assays may be used in the methods of the present technology, including but not limited to, e.g., indirect ELISA, sandwich EISA, competitive ELISA (see e.g., U.S. Pat. Nos. 5,908,781 and 7,393,843). Additionally other ELISA methods known in the art may be used in the methods of the present technology.

Other assays for use in the methods of the present technology include radioimmunoassay (RIA) (see, e.g., Weintraub, B., Principles of Radioimmunoassays, Seventh Training Course on Radioligand Assay Techniques, The Endocrine Society, (March, 1986)). The agent used to detect the polypeptide-antigen binding complex may be radioactively labeled. The radioactive isotope can be detected by means including, but not limited to, e.g., a gamma counter, a scintillation counter, or autoradiography.

In some embodiments of methods of the invention described herein, when a biomarker of an immune response directed against a component of a cancer cell of the subject, such as SOX2 or a fragment there, is detected, the level of the detected biomarker is quantified. In various embodiments, the level of the detected biomarker is then compared with the level of at least one comparator, including but not limited to a negative control, a normal control, a positive control, a historical norm, a historical control and combinations thereof. In various embodiments, the level of the detected biomarker is considered different when the level of the biomarker differs from the level of the comparator by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, or by at least 500%.

The antigens of the invention, such as SOX2 or a fragment thereof, may be used in the assays described herein, either alone or in combination with one another. The use of single antigens or any combination of antigens may be suitable for use in the assays described herein provided the assay demonstrates the desired sensitivity and negative predictive values. In certain embodiments, the use of a combination of antigens may result in an increased sensitivity value or predictive value. In some embodiments, the values are significant. Comparisons may be performed and significance determined using any of the available statistical analysis tools, alone or in combination with one another, including, for example, student's T-test, chi-square test, Fisher's exact test, analysis of variance (ANOVA), univariate statistical analyses, logistic regression analysis to calculate adjusted odds ratio (OR) and 95% confidence interval (CI). Controls for any statistically significant demographic variables that might function as confounders (e.g., gender, age, etc.) may also be utilized. Differences between values are typically considered significant at about p<0.05 or about p<0.01, for example. Other statistical analysis tools may also be used.

For instance, the assays may be performed to detect antibodies immunoreactive to only one of the antigens of the invention without assaying for antibodies reactive to any other antigen. Alternatively, the assay may be performed to detect antibodies immunoreactive to more than one of the antigens of the invention. The assays described herein may also be used with other antigens in combination with one another and/or one or more of the antigens of the invention.

In one embodiment, the invention provides compositions and methods of evaluating the relationship between the immune response directed against SOX2 and a subject's responsiveness to an immunotherapy. The present invention provides methods for determining the presence or absence of an immune response in a subject and, in turn, provides a means for predicting the likelihood of success of an immunotherapy administered to that subject. By way of non-limiting example, a subject identified as having an immune response directed against SOX2 is more likely to have a clinical response against SOX2+ cancer upon administration of an immunotherapy.

As used herein, immunotherapy refers to any therapy that leads to an increase in an immune response against cancer, such as SOX2+ cancer, in a patient. In some embodiments, the immunotherapy interferes with or blocks an existing negative signal or inhibitory signal (see Pardoll, 2012, Nature Reviews Cancer 12:252-264) that is acting to prevent or diminish the magnitude of an immune response. By way of one non-limiting example, programmed cell death protein 1 (PD1; also known as CD279) has at least two known ligands, programmed cell death 1 ligand 1 (PD-L1; also known as CD274 and B7-H1) and programmed cell death 1 ligand 2 (PD-L2; also known as CD273 and B7-DC). The interaction between PD1, expressed on immune effector cells, and one or more of its ligands results in decreased immune activity of the immune effector cells. Thus, in some embodiments of the invention, the immunotherapy relates to the therapeutic intervention of signaling through PD1, by interfering with the interaction of PD1 with at least one of its ligands, and/or by inhibiting at least one of PD1, PD-L1, PD-L2, and combinations thereof. Thus, the therapeutic intervention of signaling through PD1 serves to enhance T-cell mediated immune responses, such as those directed against cancer, such as SOX2+ cancer. Such a therapeutic intervention is referred to at times in the literature as a PD1 blockade.

In various embodiments, the therapeutic intervention of signaling through PD1 includes a small molecule drug, a polypeptide or an antibody that interferes with the interaction of PD1 with at least one of its ligands, and/or inhibits at least one of PD1, PD-L1 and PD-L2. Examples of compositions useful in the therapeutic intervention of signaling through PD1, through the interference or inhibition of at least one of PD1, PD-L1 and PD-L2, include, but are not limited to AMP224 (Amplimmune, Inc.), BMS936558 (nivolumab; MDX1106) (Bristol-Myers Squibb), GSK2661380 (GlaxoSmithKline), ONO4538 (Ono Pharmaceutical), CT011 (CureTech Ltd.), MK3475 (Merck), MEDI4736 (AstraZeneca), BMS936559 (Bristol-Myers Squibb), RG7446 (F. Hoffmann-La Roche Ltd.), MPDL3280A (Genentech Inc.) and MDX1105 (Bristol-Myers Squibb). Other examples of compositions useful in immunotherapy include, but are not limited to, BMS986015 (Bristol-Myers Squibb), IPH2102 (Innate Pharma SA), Ipilimumab (MDX010; MDX101) (Bristol-Myers Squibb), Tremelimumab (MedImmune LLC), IMP321 (Immutep SA) and MGA271 (Macrogenics). The skilled artisan will understand that the invention is not limited to the exemplary immunotherapies discussed herein. Further, the skilled artisan will understand that one or more immunotherapies can be administered alone or in any combination. Still further, the skilled artisan will understand that one or more immunotherapy can be administered in combination with any other type of therapy, including chemotherapy.

In various embodiments, the methods of the invention assess nucleic acids and include amplification techniques such as PCR and RT-PCR (including quantitative variants), and hybridization techniques such as in situ hybridization, microarrays, blots, and others. In various embodiments, the methods of the invention assess proteins and include binding techniques such as ELISA, immunohistochemistry, microarray and functional techniques such as enzymatic assays. In various embodiments, the methods of the invention employs techniques known in the art to detect an antigen, an antibody, or an antigen-antibody complex in a sample, including but are not limited to, immunoassays, enzyme assays, mass spectrometry, biosensors, and chromatography. Thus, the invention includes the use of any type of instrumentality to detect a desired antigen, immune effector molecule, antibody, or antigen-antibody complex in a sample. In various embodiments, an immunoassay can be an enzyme-linked immunosorbant immunoassay (ELISA), a sandwich assay, a competitive assay, a radioimmunoassay (RIA), a lateral flow immunoassay, a Western Blot, an immunoassay using a biosensor, an immunoprecipitation assay, an agglutination assay, a turbidity assay or a nephelometric assay.

The present invention also pertains to kits useful in any of the methods of the invention described herein. Such kits comprise components useful in any of the methods described herein, including for example, compositions and methods for harvesting and culturing immune cells, compositions and methods for stimulating immune cells, compositions, assays and methods for detecting and measuring immune effector molecule production, compositions, assays and methods for detecting and measuring immune cell proliferation, compositions, assays and methods for detecting and measuring the biomarkers of a cell-mediated immune response directed against SOX2, compositions, assays and methods for detecting and measuring biomarkers of a humoral immune response directed against SOX2, one or more containers (e.g., test tube, cell culture dish, cell culture plate, cell culture flask, cell culture bag) for containing a component of any of the embodiments of the invention described elsewhere herein, and instructional materials.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: T Cell Immunity to SOX2 and Response to Immunotherapy in Non-Small Cell Lung Cancer It has been shown that the presence of naturally occurring T cell immunity to SOX2 is associated with improved survival and reduced risk of clinical malignancy in patients with monoclonal gammopathies (Spisek et al., 2007, J Exp Med, 204(4):831-40). As described herein, the presence of T cell immunity to SOX2 in patients with NSCLC, including those undergoing immune-modulating therapy with anti-programmed death-1 (anti-PD1) antibody, has been examined. The present invention relates to the discovery that T cell immunity to SOX2 is detectable in nearly half of the patients with advanced NSCLC studied, and that its presence correlates with tumor regression following PD1 blockade.

The materials and methods of this experimental example are now described.

Patients

Blood samples were obtained from patients (n=35) with advanced NSCLC after obtaining informed consent approved by the Institutional Review Board. Some of these patients (n=25) were treated in a clinical trial of anti-PD1 antibody (Brahmer et al., 2012, N Engl J Med, 366(26): 2455-65). Clinical response in patients undergoing immunotherapy was evaluated using RECIST criteria.

Peptide Libraries

Libraries of overlapping peptides with sequences spanning the entire length of SOX2 and NY-ESO1 were synthesized as previously described (Spisek et al., 2007, J Exp Med, 204(4):831-40; Dhodapkar et al., 2010, Proc Natl Acad Sci USA, 107(19):8718-23). The composition and sequences of peptides in this library are noted in Table 1 and Table 2. The SOX2 library (Table 1) consisted of 86 peptides divided into 4 submixes: Pool 1: Nr. 1-22; Pool 2: Nr. 23-44; Pool 3: Nr. 45-66; Pool 4: Nr. 67-86. The NYESO1 library (Table 2) consisted of 47 peptides in 5 submixes. A pool of peptides derived from viral antigens (CEF; cytomegalovirus, Epstein Bar and influenza virus; Anaspec Inc., San Jose, Calif.) was used as a positive control.

TABLE 1

SOX2 Peptide library

| No. | Sequence | |
|---|---|---|
| 1 | HSARMYNMMETELK | (SEQ ID NO: 1) |
| 2 | RMYNMMETELKPPG | (SEQ ID NO: 2) |
| 3 | NMMETELKPPGPQQT | (SEQ ID NO: 3) |
| 4 | TELKPPGPQQTSGGG | (SEQ ID NO: 4) |
| 5 | PPGPQQTSGGGGNS | (SEQ ID NO: 5) |
| 6 | PQQTSGGGGNSTAA | (SEQ ID NO: 6) |
| 7 | SGGGGNSTAAAAGG | (SEQ ID NO: 7) |
| 8 | GGNSTAAAAGGNQK | (SEQ ID NO: 8) |

TABLE 1-continued

SOX2 Peptide library

| No. | Sequence | |
|---|---|---|
| 9 | STAAAAGGNQKNS | (SEQ ID NO: 9) |
| 10 | AAAAGGNQKNSPDRV | (SEQ ID NO: 10) |
| 11 | GGNQKNSPDRVKRPM | (SEQ ID NO: 11) |
| 12 | KNSPDRVKRPMNAFM | (SEQ ID NO: 12) |
| 13 | DRVKRPMNAFMVWSR | (SEQ ID NO: 13) |
| 14 | RPMNAFMVWSRGQRR | (SEQ ID NO: 14) |
| 15 | AFMVWSRGQRRKMA | (SEQ ID NO: 15) |
| 16 | VWSRGQRRKMAQENPK | (SEQ ID NO: 16) |
| 17 | GQRRKMAQENPKMH | (SEQ ID NO: 17) |
| 18 | RKMAQENPKMHNSEI | (SEQ ID NO: 18) |
| 19 | AQENPKMHNSEISKR | (SEQ ID NO: 19) |
| 20 | PKMHNSEISKRLGA | (SEQ ID NO: 20) |
| 21 | HNSEISKRLGAEWKL | (SEQ ID NO: 21) |
| 22 | ISKRLGAEWKLLSET | (SEQ ID NO: 22) |
| 23 | LGAEWKLLSETEKR | (SEQ ID NO: 23) |
| 24 | EWKLLSETEKRPFI | (SEQ ID NO: 24) |
| 25 | LLSETEKRPFIDEAK | (SEQ ID NO: 25) |
| 26 | TEKRPFIDEAKRLRA | (SEQ ID NO: 26) |
| 27 | PFIDEAKRLRALHMK | (SEQ ID NO: 27) |
| 28 | EAKRLRALHMKEH | (SEQ ID NO: 28) |
| 29 | KRLRALHMKEHPDYK | (SEQ ID NO: 29) |
| 30 | ALHMKEHPDYKYRPR | (SEQ ID NO: 30) |
| 31 | KEHPDYKYRPRRKTK | (SEQ ID NO: 31) |
| 32 | DYKYRPRRKTKTLMK | (SEQ ID NO: 32) |
| 33 | RPRRKTKTLMKKDKY | (SEQ ID NO: 33) |
| 34 | KTKTLMKKDKYTLPG | (SEQ ID NO: 34) |
| 35 | LMKKDKYTLPGGLLA | (SEQ ID NO: 35) |
| 36 | DKYTLPGGLLAPGG | (SEQ ID NO: 36) |
| 37 | TLPGGLLAPGGNSMA | (SEQ ID NO: 37) |
| 38 | GLLAPGGNSMASGVG | (SEQ ID NO: 38) |
| 39 | PGGNSMASGVGVGAG | (SEQ ID NO: 39) |
| 40 | SMASGVGVGAGLGAG | (SEQ ID NO: 40) |
| 41 | GVGVGAGLGAGVNQR | (SEQ ID NO: 41) |
| 42 | GAGLGAGVNQRMDSY | (SEQ ID NO: 42) |
| 43 | GAGVNQRMDSYAHM | (SEQ ID NO: 43) |
| 44 | VNQRMDSYAHMNGWS | (SEQ ID NO: 44) |
| 45 | MDSYAHMNGWSNGSY | (SEQ ID NO: 45) |
| 46 | AHMNGWSNGSYSMM | (SEQ ID NO: 46) |

TABLE 1-continued

SOX2 Peptide library

| No. | Sequence | |
|---|---|---|
| 47 | NGWSNGSYSMMQDQL | (SEQ ID NO: 47) |
| 48 | NGSYSMMQDQLGY | (SEQ ID NO: 48) |
| 49 | SYSMMQDQLGYPQH | (SEQ ID NO: 49) |
| 50 | MMQDQLGYPQHPGL | (SEQ ID NO: 50) |
| 51 | DQLGYPQHPGLNAHG | (SEQ ID NO: 51) |
| 52 | YPQHPGLNAHGAAQM | (SEQ ID NO: 52) |
| 53 | PGLNAHGAAQMQPMH | (SEQ ID NO: 53) |
| 54 | AHGAAQMQPMHRYDV | (SEQ ID NO: 54) |
| 55 | AQMQPMHRYDVSAL | (SEQ ID NO: 55) |
| 56 | MQPMHRYDVSALQY | (SEQ ID NO: 56) |
| 57 | MHRYDVSALQYNSMT | (SEQ ID NO: 57) |
| 58 | DVSALQYNSMTSSQT | (SEQ ID NO: 58) |
| 59 | LQYNSMTSSQTYMNG | (SEQ ID NO: 59) |
| 60 | SMTSSQTYMNGSPTY | (SEQ ID NO: 60) |
| 61 | SQTYMNGSPTYSMSY | (SEQ ID NO: 61) |
| 62 | MNGSPTYSMSYSQQG | (SEQ ID NO: 62) |
| 63 | PTYSMSYQQGTPGM | (SEQ ID NO: 63) |
| 64 | MSYSQQGTPGMALGS | (SEQ ID NO: 64) |
| 65 | SQQGTPGMALGSMGS | (SEQ ID NO: 65) |
| 66 | TPGMALGSMGSVVKS | (SEQ ID NO: 66) |
| 67 | ALGSMGSVVKSEASS | (SEQ ID NO: 67) |
| 68 | MGSVVKSEASSSPPV | (SEQ ID NO: 68) |
| 69 | VKSEASSSPPVVTSS | (SEQ ID NO: 69) |
| 70 | ASSSPPVVTSSSHSR | (SEQ ID NO: 70) |
| 71 | PPVVTSSSHSRA | (SEQ ID NO: 71) |
| 72 | PVVTSSSHSRAPCQA | (SEQ ID NO: 72) |
| 73 | SSSHSRAPCQAGDLR | (SEQ ID NO: 73) |
| 74 | SRAPCQAGDLRDMIS | (SEQ ID NO: 74) |
| 75 | CQAGDLRDMISMYL | (SEQ ID NO: 75) |
| 76 | GDLRDMISMYLPGA | (SEQ ID NO: 76) |
| 77 | RDMISMYLPGAEV | (SEQ ID NO: 77) |
| 78 | MIS MYLPGAEVPEPA | (SEQ ID NO: 78) |
| 79 | YLPGAEVPEPAAPSR | (SEQ ID NO: 79) |
| 80 | AEVPEPAAPSRLHMS | (SEQ ID NO: 80) |
| 81 | EPAAPSRLHMS QHY | (SEQ ID NO: 81) |
| 82 | APS RLHMS QHYQSG | (SEQ ID NO: 82) |
| 83 | RLHMS QHYQSGPVPG | (SEQ ID NO: 83) |
| 84 | SQHYQSGPVPGTAI | (SEQ ID NO: 84) |
| 85 | YQSGPVPGTAINGTL | (SEQ ID NO: 85) |
| 86 | PVPGTAINGTLPLSHM | (SEQ ID NO: 86) |

Pool 1: No. 1-22

Pool 2: No. 23-44

Pool 3: No. 45-66

Pool 4: No. 67-86

TABLE 2

NYESO-1 Peptide library

| No. | Sequence | |
|---|---|---|
| 1 | MQAEGRGTGGSTGDA | (SEQ ID NO: 87) |
| 2 | GRGTGGSTGDADGPG | (SEQ ID NO: 88) |
| 3 | GGSTGDADGPGGPGI | (SEQ ID NO: 89) |
| 4 | GDADGPGGPGIPDG | (SEQ ID NO: 90) |
| 5 | DGPGGPGIPDGPGG | (SEQ ID NO: 91) |
| 6 | GGPGIPDGPGGNAGG | (SEQ ID NO: 92) |
| 7 | IPDGPGGNAGGPGEA | (SEQ ID NO: 93) |
| 8 | PGGNAGGPGEAGATG | (SEQ ID NO: 94) |
| 9 | AGGPGEAGATGGRG | (SEQ ID NO: 95) |
| 10 | PGEAGATGGRGPRGA | (SEQ ID NO: 96) |
| 11 | GATGGRGPRGAGAAR | (SEQ ID NO: 97) |
| 12 | GRGPRGAGAARASG | (SEQ ID NO: 98) |
| 13 | PRGAGAARASGPGGG | (SEQ ID NO: 99) |
| 14 | GAARASGPGGGAPRG | (SEQ ID NO: 100) |
| 15 | ASGPGGGAPRGPHGG | (SEQ ID NO: 101) |
| 16 | GGGAPRGPHGGAASG | (SEQ ID NO: 102) |
| 17 | PRGPHGGAASGLNG | (SEQ ID NO: 103) |
| 18 | PHGGAASGLNGCCR | (SEQ ID NO: 104) |
| 19 | GAASGLNGCCRCGAR | (SEQ ID NO: 105) |
| 20 | GLNGCCRCGARGPES | (SEQ ID NO: 106) |
| 21 | CCRCGARGPESRLL | (SEQ ID NO: 107) |
| 22 | CGARGPESRLLEFYL | (SEQ ID NO: 108) |
| 23 | GPESRLLEFYLAMPF | (SEQ ID NO: 109) |
| 24 | RLLEFYLAMPFATPM | (SEQ ID NO: 110) |
| 25 | FYLAMPFATPMEAEL | (SEQ ID NO: 111) |
| 26 | MPFATPMEAELARRS | (SEQ ID NO: 112) |
| 27 | TPMEAELARRSLA | (SEQ ID NO: 113) |
| 28 | MEAELARRSLAQDA | (SEQ ID NO: 114) |

TABLE 2-continued

NYESO-1 Peptide library

| No. | Sequence | |
|---|---|---|
| 29 | ELARRSLAQDAPPL | (SEQ ID NO: 115) |
| 30 | RRSLAQDAPPLPVPG | (SEQ ID NO: 116) |
| 31 | AQDAPPLPVPGVLLK | (SEQ ID NO: 117) |
| 32 | PPLPVPGVLLKEFTV | (SEQ ID NO: 118) |
| 33 | VPGVLLKEFTVSGNI | (SEQ ID NO: 119) |
| 34 | LLKEFTVSGNILTIR | (SEQ ID NO: 120) |
| 35 | FTVSGNILTIRLTAA | (SEQ ID NO: 121) |
| 36 | GNILTIRLTAADHR | (SEQ ID NO: 122) |
| 37 | LTIRLTAADHRQLQL | (SEQ ID NO: 123) |
| 38 | LTAADHRQLQLSISS | (SEQ ID NO: 124) |
| 39 | DHRQLQLSISSCL | (SEQ ID NO: 125) |
| 40 | RQLQLSISSCLQQLS | (SEQ ID NO: 126) |
| 41 | LSISSCLQQLSLLMW | (SEQ ID NO: 127) |
| 42 | SCLQQLSLLMWI | (SEQ ID NO: 128) |
| 43 | LQQLSLLMWITQCF | (SEQ ID NO: 129) |
| 44 | LSLLMWITQCFLPVF | (SEQ ID NO: 130) |
| 45 | MWITQCFLPVFLA | (SEQ ID NO: 131) |
| 46 | ITQCFLPVFLAQPPS | (SEQ ID NO: 132) |
| 47 | FLPVFLAQPPSGQRR | (SEQ ID NO: 133) |

Pool 1: No. 1-10

Pool 2: No. 11-20

Pool 3: No. 21-30

Pool 4: No. 31-40

Pool 5: No. 41-47

Sox2 Amino Acid Sequence (SEQ ID NO: 134)
HSARMYNMMETELKPPGPQQTSGGGGGNSTAAAAGGNQKNSPDRVKRPM

NAFMVWSRGQRRKMAQENPKMHNSEISKRLGAEWKLLSETEKRPFIDEA

KRLRALHMKEHPDYKYRPRRKTKTLMKKDKYTLPGGLLAPGGNSMASGV

GVGAGLGAGVNQRMDSYAHMNGWSNGSYSMMQDQLGYPQHPGLNAHGAA

QMQPMHRYDVSALQYNSMTSSQTYMNGSPTYSMSYSQQGTPGMALGSMG

SVVKSEASSSPPVVTSSSHSRAPCQAGDLRDMISMYLPGAEVPEPAAPS

RLHMSQHYQSGPVPGTAINGTLPLSHM

Detection of Antigen-Specific T Cells

The presence of SOX2, NYESO1 and CEF-reactive T cells was detected based on antigen-dependent cytokine production and proliferation, as described (Spisek et al., 2007, J Exp Med, 204(4):831-40; Dhodapkar et al., 2010, Proc Natl Acad Sci USA, 107(19):8718-23). Briefly, peripheral blood mononuclear cells (PBMCs) were isolated using Ficoll Hypaque. Freshly isolated PBMCs ($2.5 \times 10^5$ cells/well) were either cultured alone (control) or with peptide pools from SOX2, NYESO1 or CEF peptides at 3 µg/ml in 5% PHS in 96 well round bottom plates. PHA was used as a positive control. After 48 hours in culture, the culture supernatant was harvested and examined for the presence of IP10 (interferon γ-induced protein 10) using a luminex assay as per the manufacturers protocol. Values ≥2 fold over the negative control were deemed positive based on analysis of inter and intra-assay variation as previously described (Spisek et al., 2007, J Exp Med, 204(4):831-40; Dhodapkar et al., 2010, Proc Natl Acad Sci USA, 107(19):8718-23). In some patients, the T cell reactivity to a specific peptide within the SOX2 mix was confirmed by stimulating PBMCs with single peptides from that mix.

Antigen-Dependent Proliferation Assay

The presence of antigen-dependent proliferation was monitored using a CFSE dilution assay as previously described (Dhodapkar et al., 2010, Proc Natl Acad Sci USA, 107(19):8718-23). Freshly isolated PBMCs were labeled with CFSE cell tracker dye (0.5 µM; Molecular Probes) and cultured with 1 µg/mL of anti-CD28 and anti-CD49d (BD Biosciences) alone or with SOX2 peptide mixes (5 µg/mL), CEF mix (3 µg/mL), or PHA (2 µg/mL). After 7 days of culture, PBMCs were stained with anti-CD3; CD4; CD8 and T-cell proliferation was analyzed using the FACSCalibur (Becton Dickinson). The data were analyzed using the FlowJo software.

Detection of Antibodies Against SOX2 and EBNA

The presence of antibodies against SOX2 or EBV nuclear antigen EBNA1 was analyzed using an ELISA as described (Spisek et al., 2007, J Exp Med, 204(4):831-40). SOX2 full length protein (Abcam) was used to coat ELISA plate (25 µl/well at 1 mg/ml concentration) for 2 hours at room temperature. The plate was washed twice with PBS with tween and blocked overnight with 4% NF milk at 4° C. Patient plasma was diluted 1:100 and 1:400 in 4% NF milk and 200 µl of diluted plasma was added to each well of the ELISA plate and incubated for 2 hours at room temperature. The plates were than washed and probed with goat anti-human IgG-HRP (1:6000; Southern Biotech) in 5% NF milk for 1 hour at room temperature. Finally, 30 µl of substrate was added to each plate for 15 minutes followed by stop solution (both from Biosource). The ELISA was read at 450 nm using an ELISA plate reader. Antibodies against EBNA were detected using a commercial ELISA kit (Scimedx) using the manufacturers protocol.

Immunohistochemistry for Detection of SOX2 Expression

Parafin sections from lung cancer tissue were subjected to antigen retrieval at low pH with citrate buffer. Slides were then stained with anti-human SOX2 antibody (1:100, mouse monoclonal, clone 245610, R&D), followed by Envision anti-mouse antibody (Dako) as a secondary antibody.

Statistical Analysis

Data from different groups was compared using a Students' T test or a non-parametric test (Mann Whitney). P value was set at 0.05 for significance.

The results of this experimental example are now described.

Predictors of Responsiveness to Therapy

Recent studies have heightened the need for predictors of responsiveness to immune-therapy in non-small cell lung cancer (NSCLC). Embryonal stem-cell gene SOX2 has been implicated in the pathogenesis of NSCLC. Anti-SOX2 T cell responses were detected in over half the patients with advanced NSCLC. Patients with SOX2 immunity were more likely to benefit from anti-programmed death1 (PD1) antibody than those without (28.5% vs 0%, p<0.01), and achieve durable responses. Cellular or antibody responses to viral, or another tumor antigen (NYESO1), were not predictive. Immune therapy led to epitope spread with increasing immune-reactivity. Thus, these data demonstrate SOX2 is an important biomarker and target for immunotherapy in NSCLC.

Figure 1B:
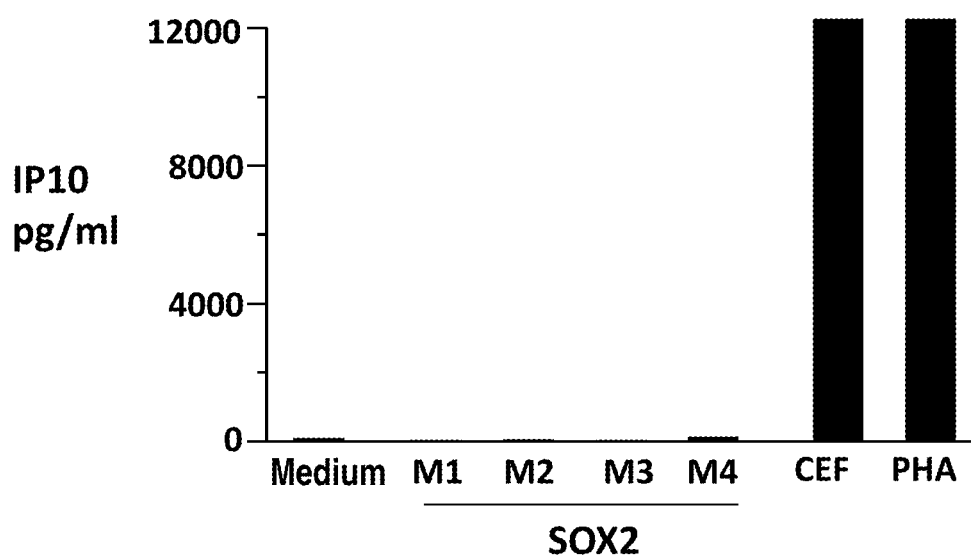
Figure 1C:
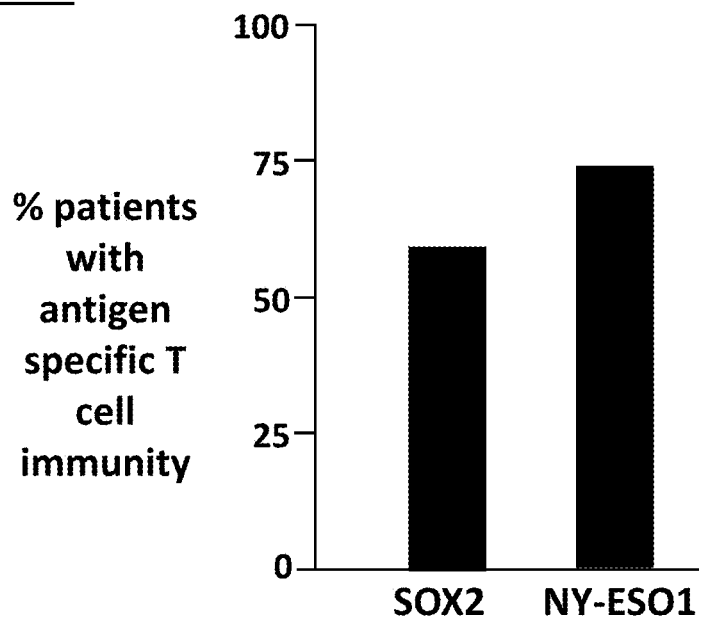
Figure 1D:
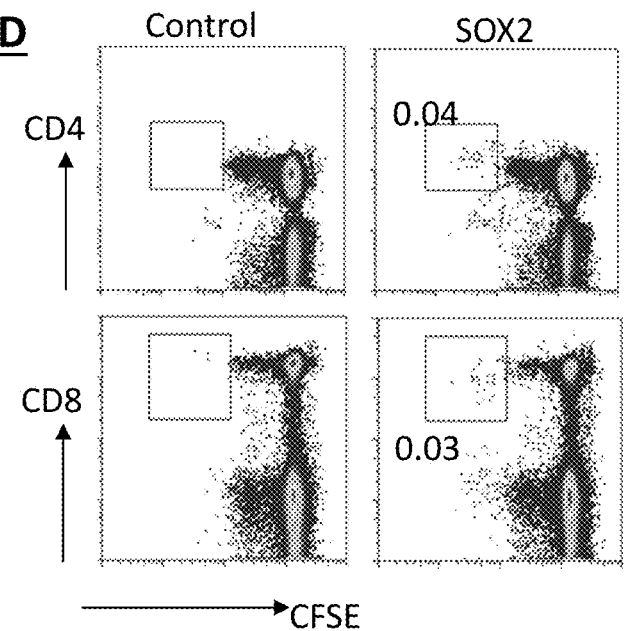
Figure 1E:
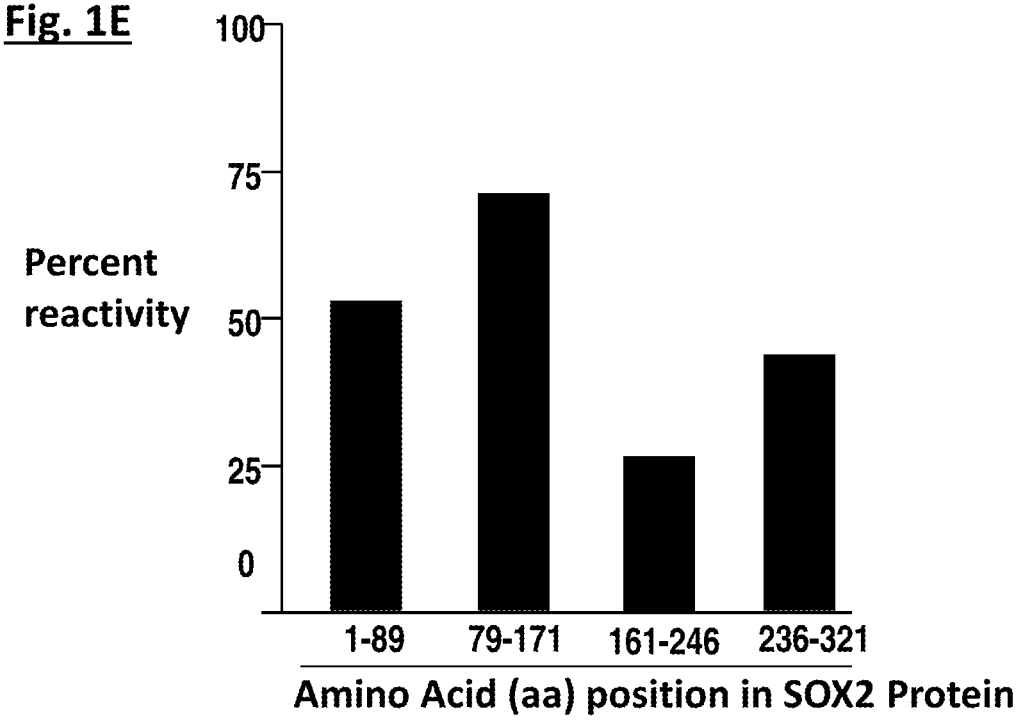
Figure 1F:
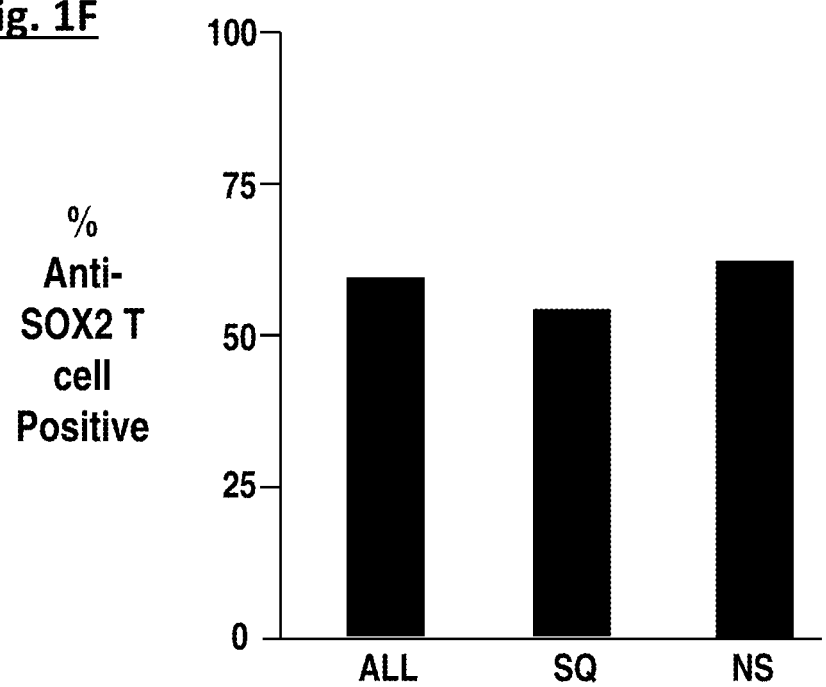
Figure 1G:
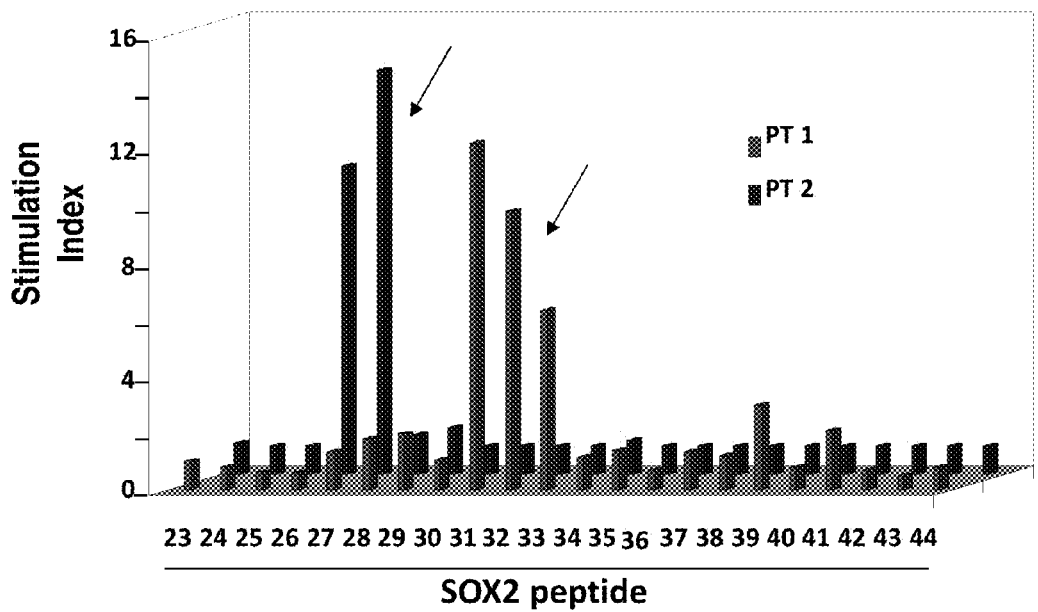
Figure 1H:
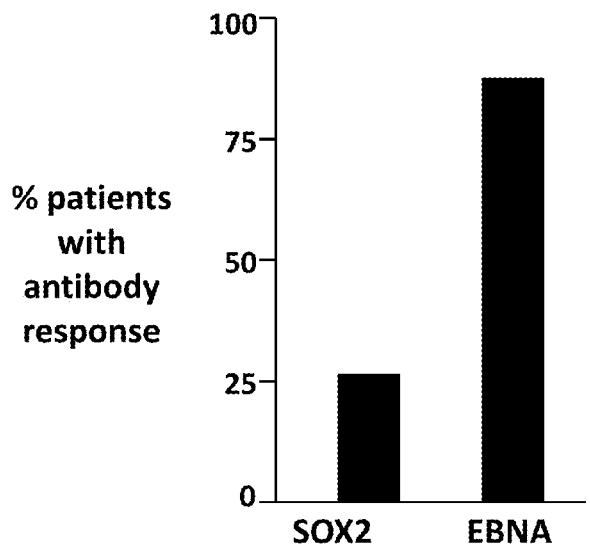

The presence of immunity to SOX2 in freshly isolated peripheral blood mononuclear cells (PBMCs) from patients with advanced NSCLC using an overlapping peptide library spanning the entire protein was analyzed, as previously described (Spisek et al., 2007, J Exp Med, 204(4):831-40), or with PHA as a positive control (FIGS. 1A-1B). Immunity to NYESO1 was also monitored as a known tumor antigen in lung cancer and a target of autoreactivity (Jungbluth et al., 2001, Int J Cancer, 92(6):856-60; Lee et al., 1999, Cancer J Sci Am, 5(1):20-5; Isobe et al., 2009, Cancer Immun, 9:8; Danke et al., 2004, J Immunol, 172(10):5967-72). Overall, immunity to SOX2 and NY-ESO-1 was detected in 21/35 (60%) and 17/23 (74%) of the patients tested, respectively (FIG. 1C). The presence of SOX2-reactive T cells was also confirmed using a CFSE dilution assay, and found to consist of both CD4+ T cells and CD8+ T cells (FIG. 1D). Immune reactivity was detected against peptides derived from throughout the SOX2 protein (FIG. 1E), with some preference towards the N-terminus, and was detected in patients with both squamous or non-squamous histology (FIG. 1F). In order to further confirm the fine specificity of the peptides within the reactive submix, peptides from the reactive submix were tested individually, allowing the determination of the peptide/region of reactivity (FIG. 1G). The presence of antibodies against SOX2 using an ELISA based assay was also examined. The presence of anti-SOX2 antibodies was detected in 7 of 25 (28%) patients tested, consistent with other studies (Gure et al., 2000, Proc Natl Acad Sci USA, 97(8):4198-203) (FIG. 1H). As a control, the presence of EBNA-specific antibodies could be detected in the majority of patients (22 of 25, 88%). Together, these data demonstrate that SOX2 is a common target of endogenous T cell immunity in patients with NSCLC.

Figure 2A:
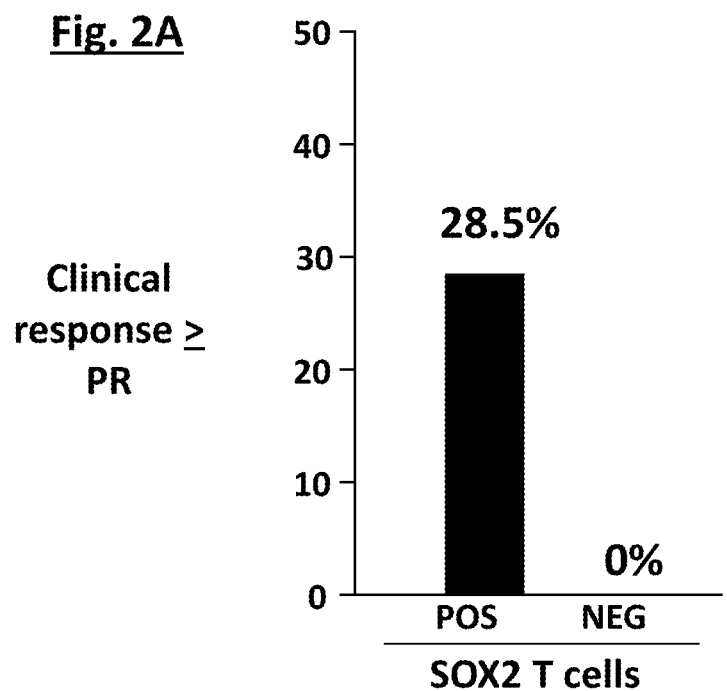
FIGS. 2A-2F depict the results of experiments examining the correlation between endogenous antigen-specific immunity and response to PD1 blockade in lung cancer.
Figure 2B:
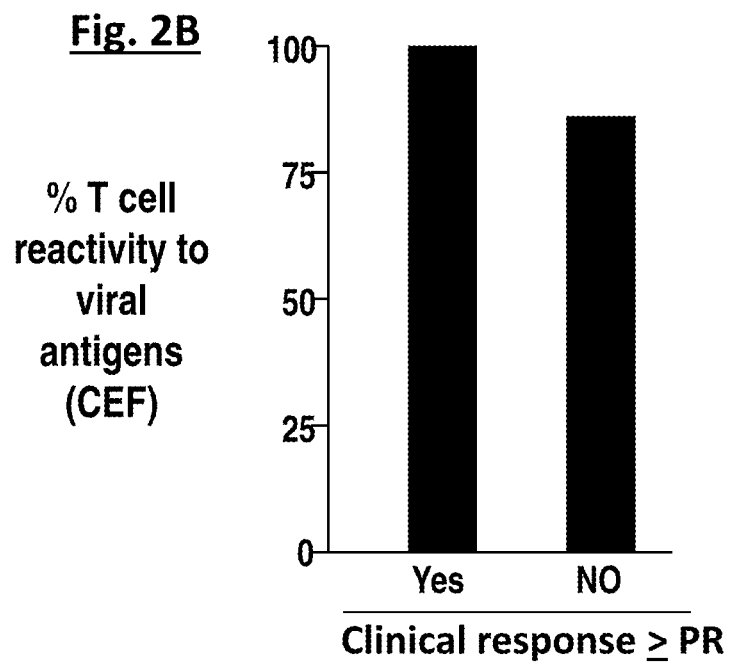
Figure 2C:
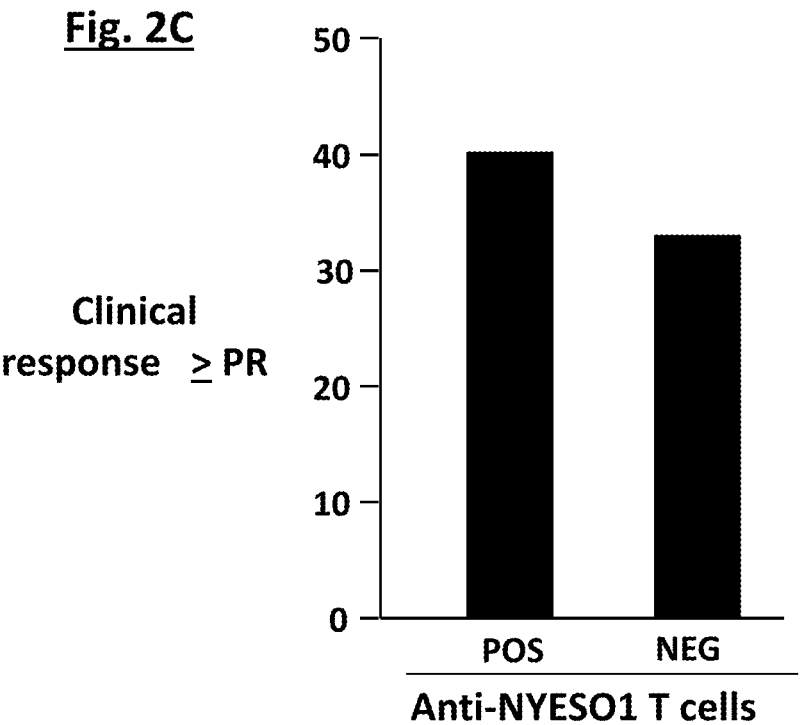

Several of the patients studied for SOX2 immunity were treated in a clinical trial with anti-PD1 antibody (n=25) (Brahmer et al., 2012, N Engl J Med, 366(26):2455-65). Therefore, the correlation between T cell immunity to SOX2 and outcome following PD1 blockade was analyzed. Of 23 patients analyzed for SOX2 T cell immunity at baseline (or within cycle 1), 4 of 14 (28.5%) with anti-SOX2 T cells achieved an objective response (≥PR) to therapy. In contrast, there were no responses in the 9 patients lacking immunity to SOX2 (FIG. 2A). The lack of SOX2 immunity in these patients was not due to general immune paresis, as both cohorts of patients had comparable immune reactivity to viral antigens (as measured using cocktail of antigens derived from CMV, EBV and influenza; CEF) (FIG. 2B). As another control, T cell immunity to another tumor-associated antigen NY-ESO1 did not correlate with clinical response to PD1 blockade (FIG. 2C).

Figure 2D:
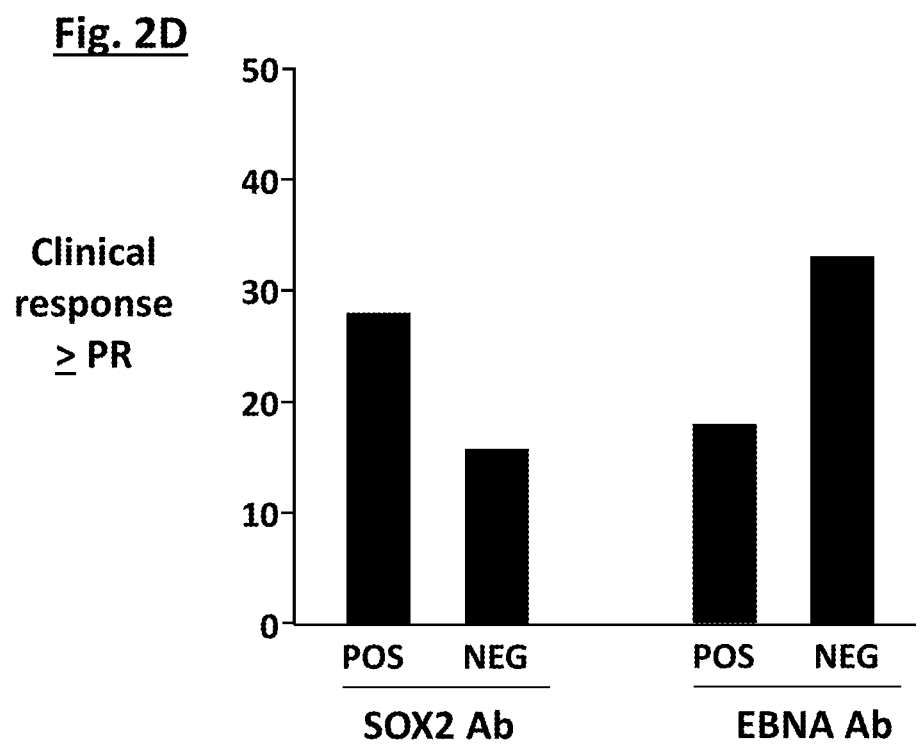
Figure 2E:
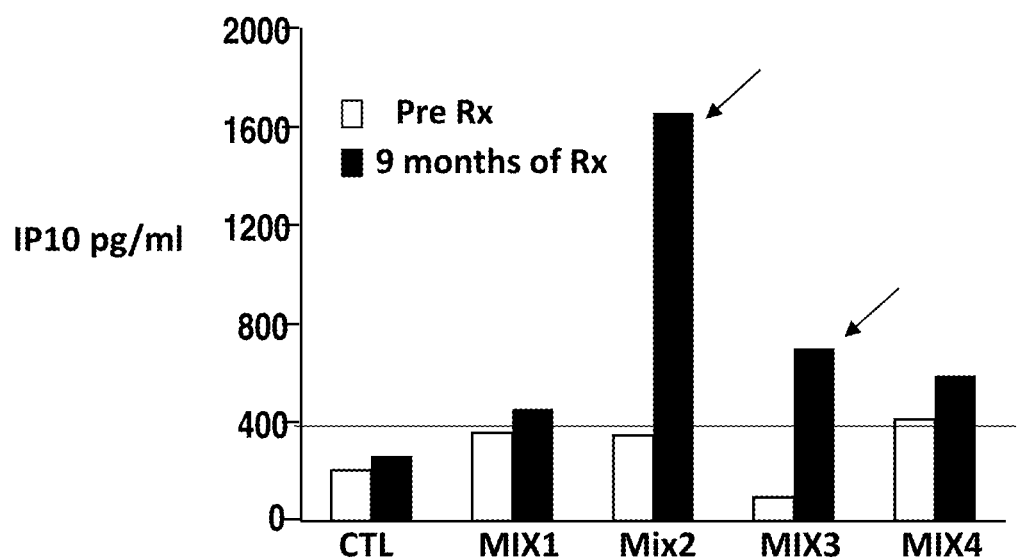

Some studies have previously tracked antibody responses to NY-ESO1 in melanoma patients treated with anti-CTLA4 antibody in melanoma, presumably as a surrogate for CD4+ T cell responses (Yuan et al., 2011, Proc Natl Acad Sci USA, 108(40):16723-8). However even in these settings, T cell responses were found to correlate better with clinical response than antibodies (Yuan et al., 2011, Proc Natl Acad Sci USA, 108(40):16723-8). Antibody responses to SOX2 were detected in only 7/25 (28%) patients. Neither the presence of antibodies against SOX2 or against EBNA1 correlate with clinical response to PD1 blockade (FIG. 2D). Antibody-mediated lysis of tumor cells can in principle lead to further amplification of immune response via cross-presentation of antigens from dying cells. Analysis of serial samples collected in patients demonstrated that at least in some patients, clinical response to PD1 blockade was associated with evolution of reactivity against new regions of the protein, indicating the induction of intra-molecular epitope spread (FIG. 2E). This also included 2 patients who lacked anti-SOX2 immunity at baseline, but then developed detectable responses over time. The two patients who had SOX2 T cell immunity at baseline and developed epitope spreading had partial responses and continue to remain on therapy 19 and 15 months since starting therapy. One of the two patients who had a late conversion had stabilization of his disease following initial progression and remains on therapy for 15 months. The second converter had progressive disease and was taken off study 3 months after starting therapy.

Figure 2F:
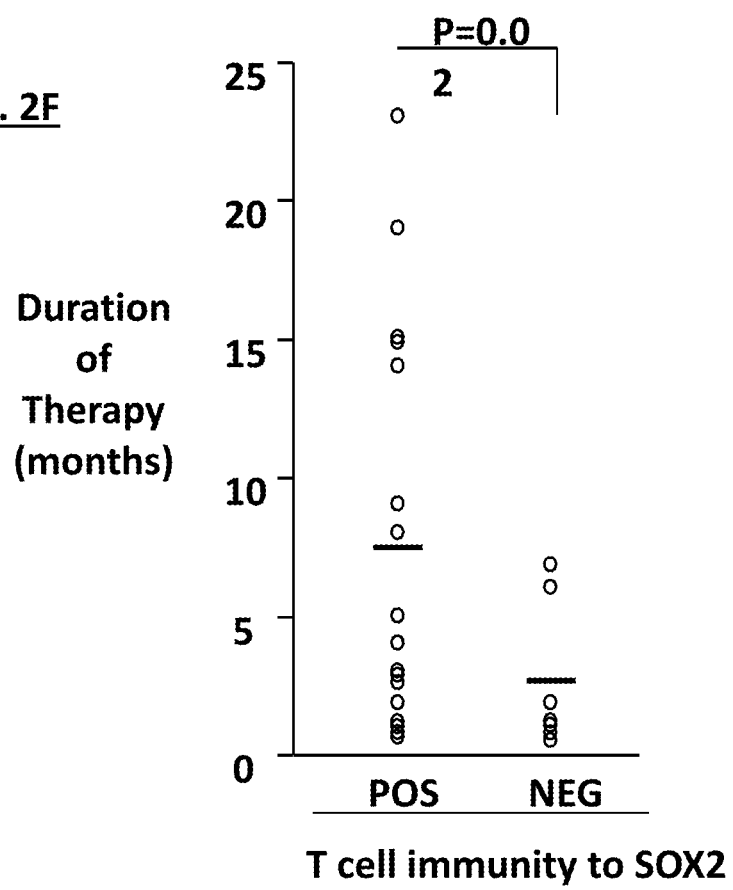
Figure 3A:
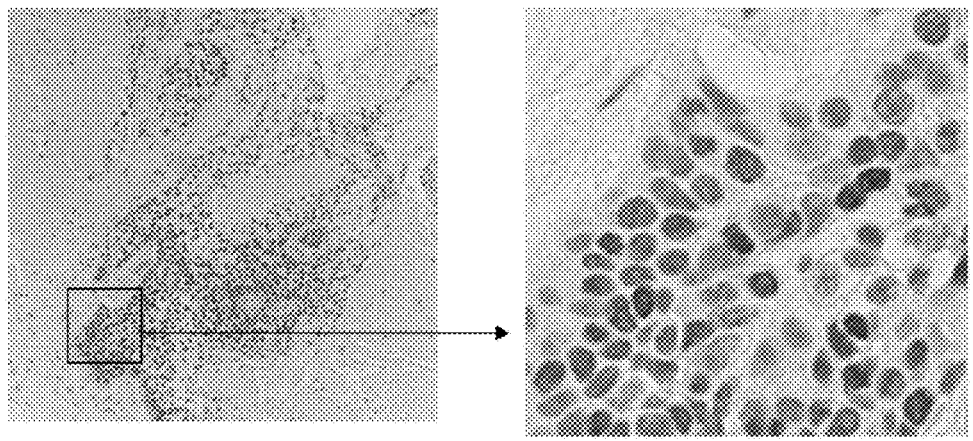
FIGS. 3A-3D depict images showing expression of SOX2 in human lung cancer. SOX2 expression was determined on the tumor tissue from paraffin embedded tumor sections.
Figure 3B:
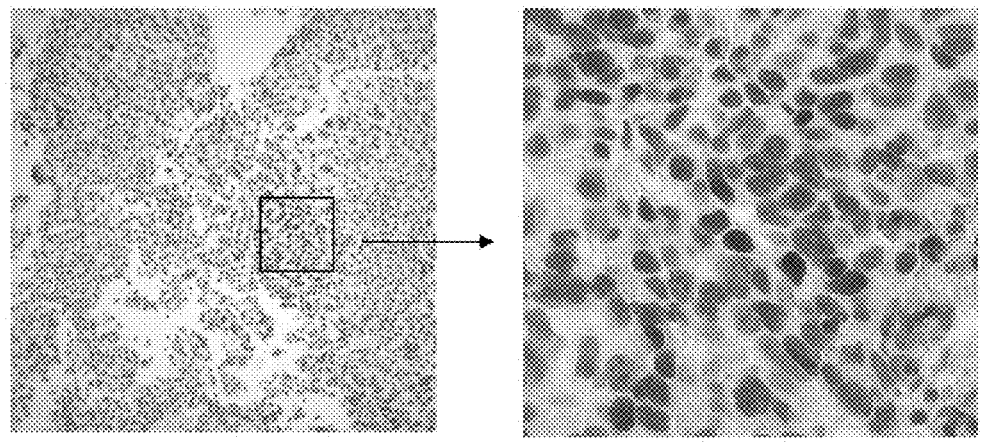
Figure 3C:
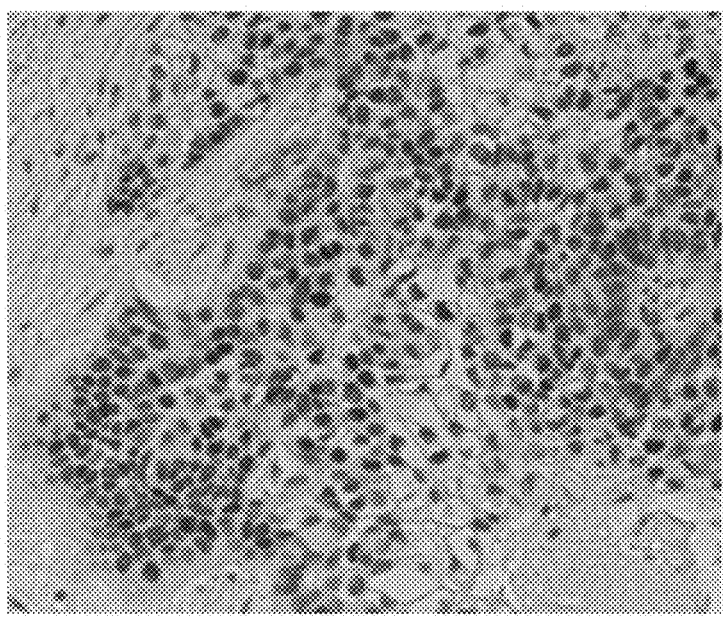
Figure 3D:
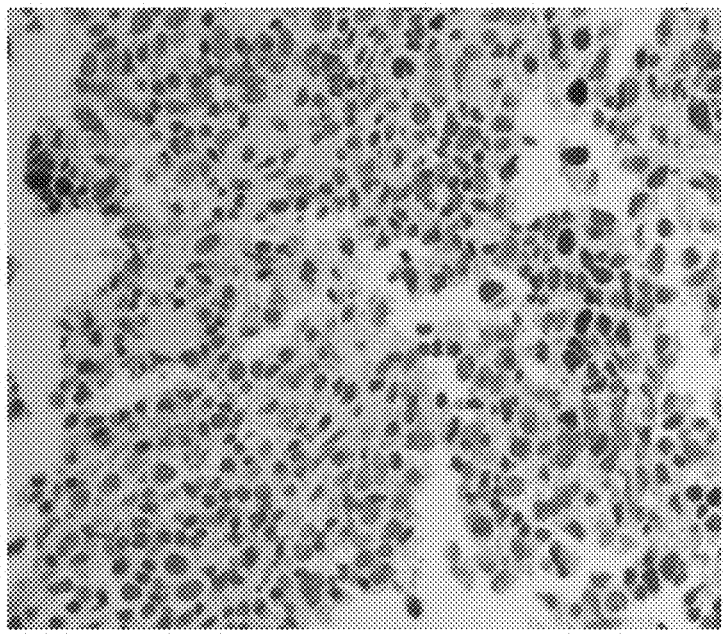

Patients who benefit from immune therapies might not be restricted to those who achieve objective tumor regressions, as prolonged periods of stability may also be valuable. Therefore, the duration of anti-PD1 therapy in patients with or without SOX2 immunity was also evaluated. The mean duration of therapy in patients with SOX2 immunity was longer than those without such responses (7.5 months vs. 2.6 months, p=0.02; FIG. 2F).

In summary, it has been shown that patients with advanced NSCLC can mount an endogenous T cell response to SOX2 and that the presence of these responses correlates with improved outcome following therapy with anti-PD1 antibody. These data are consistent with preclinical studies that tumor regressions following T cell checkpoint blockade depend on preexisting immunity and the nature of antigenic target of the immune response (van Elsas et al., 2001, J Exp Med, 194(4):481-9). Endogenous tumor immunity may itself lead to the induction of PDL1 in melanoma (Taube et al., 2012, Sci Transl Med, 4(127):127ra37), although this remains to be demonstrated in lung cancer. Expression of membranous PDL1 on tumor cells was recently proposed as a biomarker predictive of response to anti-PD1 therapy (Brahmer et al., 2012, N Engl J Med, 366(26):2455-65). However, very few patients with lung cancer were studied in Brahmer. Further, such as study requires the availability of adequate tumor tissue and is subject to challenges of heterogenous expression of this marker.

The data described herein demonstrate the detection of anti-SOX2 T cells as an effective biomarker to identify patients more likely to benefit from PD1 blockade in lung cancer, and to monitor the effects of therapy. Similarly, patients found to be lacking in such responses can be identified as candidates for a vaccine against this antigen, prior to PD1 blockade. A recent study suggested improved survival in SOX2-expressing squamous cell lung cancers (Wilbertz et al., 2011, Mod Pathol, 24(7):944-53). As described herein, the expression of SOX2 is greater in squamous than non-squamous histologies of NSCLC, but is heterogenous (FIGS. 3A-3D). However, the finding that the anti-SOX2 T cells can be detected in both types of NSCLC is consistent with the explanation that the expression of SOX2 in bulk tumor may not be a good surrogate for the presence of endogenous immunity to this antigen. Heterogeneity of SOX2 expression may also create challenges with sampling artifacts related to limited core biopsies.

The potential importance of this antigen in NSCLC may relate to its role as a lineage survival oncogene or in regulating the biology of cancer stem cells (Bass et al., 2009, Nat Genet, 41(11):1238-42; Hussenet & Manoir, 2010, Cell Cycle, 9(8):Epub; Yuan et al., 2010, PLoS One, 5(2):e9112;

Lu et al., 2011, PLoS One, 5(6):e11022; Kim et al., 2005, Cell, 121(6):823-35; Leung et al., 2011, PLoS One, 5(11): e14062; Tompkins et al., 2009, PLoS One, 4(12):e8248; Nakatsugawa et al., 2011, Lab Invest, 91(12):1796-804; Xiang et al., 2011, Br J Cancer, 104(9):1410-7. As SOX2 represents an early genomic alteration in NSCLC, this may also point to the importance of targeting proximate pathways for durable responses in cancer (McCaughan et al., 2010, Am J Respir Crit Care Med, 182(1):83-91). Immune system modulation may be a particularly attractive approach to targeting this antigen, as human T cells are capable of recognizing several epitopes derived from this antigen (Spisek et al., 2007, J Exp Med, 204(4):831-40; Dhodapkar & Dhodapkar, 2011, Cancer J, 17(5):397-402). SOX2 and other pluripotency pathways are emerging as a potential target in several human cancers (Dhodapkar et al., 2010, Proc Natl Acad Sci USA, 107(19):8718-23; Dhodapkar & Dhodapkar, 2011, Cancer J, 17(5):397-402; Dhodapkar, 2010, Curr Opin Immunol, 22(2):245-50). Harnessing immunity directed against these genes and gene products may be beneficial in diverse human tumors.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of identifying and treating a subject with non-small cell lung cancer (NSCLC) comprising a (sex determining region Y)-box 2-positive (SOX2-positive) T-cell, the method comprising:

assaying a reaction system comprising a biological sample from the NSCLC subject, wherein the biological sample comprises a T cell from the subject, and a set of overlapping peptides that span a SOX2 protein region selected from the group consisting of: (a) amino acids 1-89 of SEQ ID NO:134; (b) amino acids 79-171 of SEQ ID NO:134; (c) amino acids 161-246 of SEQ ID NO:134; and (d) amino acids 236-321 of SEQ ID NO:134;

for: (i) at least one T cell response biomarker generated by the T cell in response to the set of overlapping peptides, wherein the at least one T cell biomarker is at least one selected from the group consisting of IFN-γ and IP10, or (ii) proliferation of the T cell in response to the set of overlapping peptides, wherein:

when in (i) the amount of the at least one T cell response biomarker in the reaction system is higher than in an otherwise identical control reaction system that lacks the set of overlapping peptides or in (ii) proliferation of the T cell in the reaction mixture is higher than in an otherwise identical control reaction system that lacks the set of overlapping peptides, the biological sample from the subject comprises a SOX2-positive T cell, and, administering to the subject immunotherapy for cancer, wherein the immunotherapy comprises at least one selected from the group consisting of a PD1 blockade immunotherapy and a CTLA-4 blockade immunotherapy, wherein the PD1 blockade immunotherapy comprises at least one selected from the group consisting of AMP224, BMS936558, GSK2661380, ONO4538, CT011, MK3475, MEDI4736, BMS936559, RG7446, MPDL3280A, and MDX1105.

2. The method of claim 1, wherein the assaying comprises at least one assay selected from the group consisting of flow cytometry, immunocytochemistry, immunohistochemistry, ELISPOT, ELISA and variations thereof.

3. The method of claim 1, wherein the set of overlapping peptides is selected from the group consisting of:
  (a) a mixture of each SOX2 fragment from the group consisting of SEQ ID NOs:1-22, which spans the SOX2 protein region corresponding to amino acids 1-89 of SEQ ID NO:134;
  (b) a mixture of each SOX2 fragment from the group consisting of SEQ ID NOs:23-44, which spans the SOX2 protein region corresponding to amino acids 79-171 of SEQ ID NO:134;
  (c) a mixture of each SOX2 fragment from the group consisting of SEQ ID NOs:45-66, which spans the SOX2 protein region corresponding to amino acids 161-246 of SEQ ID NO:134; and
  (d) a mixture of each SOX2 fragment from the group consisting of SEQ ID NOs:67-86, which spans the SOX2 protein region corresponding to amino acids 236-321 of SEQ ID NO:134.

4. The method of claim 1, wherein the at least one biomarker is detected and the at least one biomarker's level is quantified.

5. The method of claim 1, wherein in (i) the amount of the at least one T cell response biomarker in the reaction system is higher than in an otherwise identical control reaction system that lacks the set of overlapping peptides, or in (ii) proliferation of the T cell in the reaction mixture is higher than in an otherwise identical control reaction system that lacks the set of overlapping peptides, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, or by at least 500%.

6. The method of claim 1, wherein the biological sample is at least one selected from the group consisting of blood, serum, plasma, lymph and tumor tissue.

7. The method of claim 1, wherein the biological sample comprises at least one selected from the group consisting of peripheral blood lymphocyte and peripheral blood mononuclear cell.

8. The method of claim 1, wherein the at least one T cell response biomarker is detected using an antibody or antibody fragment that specifically binds to the at least one T cell response biomarker.

* * * * *